United States Patent
Saul et al.

(10) Patent No.: US 10,113,009 B2
(45) Date of Patent: *Oct. 30, 2018

(54) METHODS FOR MAKING SACCHARIDE-PROTEIN GLYCOCONJUGATES

(71) Applicant: GlaxoSmithKline Biologicals SA, Rixensart (BE)

(72) Inventors: Allan James Saul, Castellina (IT); Francesca Micoli, Florence (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/150,302

(22) Filed: May 9, 2016

(65) Prior Publication Data
US 2016/0297895 A1 Oct. 13, 2016

Related U.S. Application Data

(63) Continuation of application No. 14/343,351, filed as application No. PCT/IB2012/054805 on Sep. 14, 2012, now Pat. No. 9,358,284.

(60) Provisional application No. 61/534,751, filed on Sep. 14, 2011.

(51) Int. Cl.
| | |
|---|---|
| *C08B 37/00* | (2006.01) |
| *C07K 16/12* | (2006.01) |
| *C07K 16/44* | (2006.01) |
| *A61K 39/112* | (2006.01) |
| *A61K 39/095* | (2006.01) |
| *A61K 39/02* | (2006.01) |
| *A61K 39/385* | (2006.01) |
| *C07K 14/34* | (2006.01) |
| *A61K 47/64* | (2017.01) |
| *A61K 39/00* | (2006.01) |

(52) U.S. Cl.
CPC .......... *C08B 37/0006* (2013.01); *A61K 39/02* (2013.01); *A61K 39/0275* (2013.01); *A61K 39/095* (2013.01); *A61K 39/385* (2013.01); *A61K 47/646* (2017.08); *A61K 47/6415* (2017.08); *C07K 14/34* (2013.01); *C07K 16/1285* (2013.01); *C07K 16/44* (2013.01); *C08B 37/0003* (2013.01); *C08B 37/006* (2013.01); *C08B 37/0063* (2013.01); *C08B 37/0081* (2013.01); *A61K 2039/6037* (2013.01); *C07K 2317/734* (2013.01)

(58) Field of Classification Search
None
See application file for complete search history.

(56) References Cited

U.S. PATENT DOCUMENTS

| | | |
|---|---|---|
| 6,087,328 A | 7/2000 | Lees |
| 6,645,503 B1 | 11/2003 | Arumugham et al. |
| 2004/0170638 A1* | 9/2004 | Mistretta .............. A61K 39/092 424/184.1 |
| 2007/0134197 A1* | 6/2007 | Eichner .............. A61K 38/1816 424/85.1 |
| 2007/0141084 A1 | 6/2007 | Lee et al. |
| 2009/0043077 A1 | 2/2009 | Berti |

FOREIGN PATENT DOCUMENTS

| | | |
|---|---|---|
| EP | 0 477 508 A1 | 4/1992 |
| WO | WO 01/78787 A2 | 10/2001 |
| WO | WO 2011/080595 A2 | 7/2011 |

OTHER PUBLICATIONS

Taylor et al., "Synthesis, Charaterization, and Clinical Evaluation of Conjugate Vaccines Composed of the O-Specific Polysaccharides of Shigella dysenteriae Type 1, Shigella flexneri Type 2a, and Shigella sonnei (Plesiomonas shigelloides) Bound to Bacterial Toxoids", Infection and Immunity, vol. 61, No. 9, Sep. 1993, pp. 3678-3687.
Chem 4563, Organic Qualitative Analysis Solubility Tests, faculty. swosu.edu/william.kelly/pdf/qo3.pdf, downloaded from the internet May 29, 2015.
Mawas, Infection and Immunity, Sep. 2002, p. 5107-5114, vol. 70, No. 9.

(Continued)

*Primary Examiner* — Layla D Berry
(74) *Attorney, Agent, or Firm* — Birch, Stewart, Kolasch & Birch, LLP

(57) ABSTRACT

The invention provides a process for the reductive amination of a carbonyl group at the reducing terminus of a polysaccharide, wherein the reductive amination is carried out at a pH between 4 and 5. The invention also provides a process for preparing a conjugate of a polysaccharide and a carrier molecule, comprising the steps of: (a) coupling the polysaccharide to a linker, to form a polysaccharide-linker compound in which the free terminus of the linker is an ester group; and (b) reacting the ester group with a primary amine group in the carrier molecule, to form a polysaccharide-linker-carrier molecule conjugate in which the linker is coupled to the carrier molecule via an amide linkage. The invention also provides a process for reducing contamination of a polysaccharide-linker compound with unreacted linker, comprising a step of precipitating unreacted linker under aqueous conditions at a pH of less than 5. The invention also provides polysaccharide-linker-carrier molecule conjugates and intermediate compounds obtained or obtainable by these processes.

13 Claims, 9 Drawing Sheets

(56) References Cited

OTHER PUBLICATIONS

Meikle, Glycoconjugate J (1990) 7:207-218.
Solubility Tests for Unknowns, http://www2.ups.edu/courses/organicchemlab/c250lab.10/aqsolubility.htm, downloaded from the internet May 29, 2015.

* cited by examiner

1. Marker
2. CRM$_{197}$
3. MenX-CRM$_{197}$ conj. mixture

METHODS FOR MAKING SACCHARIDE-PROTEIN GLYCOCONJUGATES

CROSS REFERENCE TO RELATED APPLICATIONS

This application is a Continuation of U.S. patent application Ser. No. 14/343,351, with an international filing date of Sep. 14, 2012, which is the U.S. National Phase of International Patent Application No. PCT/IB2012/054805, filed Sep. 14, 2012, which claims priority to U.S. Provisional Patent Application No. 61/534,751, filed Sep. 14, 2011, the disclosures of which are herein incorporated by reference in their entirety.

TECHNICAL FIELD

This invention is in the field of conjugating saccharides, particularly the core domain from the lipopolysaccharide of Gram-negative bacteria, to carriers in order to form glycoconjugates. The glycoconjugates are useful for immunisation.

BACKGROUND ART

Saccharides from bacteria have been used for many years in vaccines. As saccharides are T-independent antigens, however, they are poorly immunogenic. Conjugation to a carrier can convert T-independent antigens into T-dependent antigens, thereby enhancing memory responses and allowing protective immunity to develop. The most effective saccharide vaccines are therefore based on glycoconjugates, and the prototype conjugate vaccine was against *Haemophilus influenzae* type b ('Hib') [e.g. see chapter 14 of ref. 64].

Gram-negative bacteria are surrounded by an outer membrane that contains lipopolysaccharide. Lipopolysaccharides are a diverse group of molecules that act as endotoxins and elicit strong immune responses in mammals. Each lipopolysaccharide comprises three parts: an O-antigen (also referred to as the O-specific polysaccharide or O-polysaccharide), a core domain, and a lipid A domain. Antibodies against the O-antigen from a particular Gram-negative bacterium may confer protection against infection by that bacterium. Vaccines have therefore been envisaged that contain O-antigens conjugated to carrier proteins. For example, O-antigen-based conjugate vaccines have been proposed for various Salmonellae (e.g. serovars *Salmonella Typhimurium* and *Salmonella Paratyphi* A of *Salmonella enterica* in ref. 1 and 2); *Shigella* species [ref. 3, 4, 5, 6, 7, 8 and 9]; and *Escherichia coli* [ref. 10 and 11]. In these vaccines, the O-antigen is linked to the core domain from the full-length lipopolysaccharide (i.e. the conjugated polysaccharide is a lipopolysaccharide without its lipid A domain). The polysaccharide is conjugated to the carrier via its core domain. This core domain may itself induce protective antibodies, and conjugate vaccines have therefore been envisaged that contain a core domain that is not linked to an O-antigen [ref. 12].

Various methods are known for the conjugation of core domain-containing polysaccharides to a carrier protein. Some methods involve random activation of the polysaccharide chain (e.g. with cyanogen bromide (CNBr) or 1-cyano-4-dimethylaminopyridinium tetrafluoroborate (CDAP)) prior to conjugation via a linker (see, for example, ref. 1 and 2). Other methods are more selective, involving a specific residue on the chain (e.g. the 2-keto-3-deoxyoctanoic acid (KDO) terminus of the core domain). For example, methods in reference 13 involve reductive amination between the carbonyl group in the KDO terminus with adipic acid dihydrazide (ADH) linker. Reactions involving reductive amination are typically very slow, e.g. the 7-day step in ref. 13. Another selective method is described in ref. 9, this time involving coupling via the carboxyl group in KOO using 1-ethyl-1-3-(3-dimethylaminopropyl)carbodiimide (EDAC) and ADH. In these non-selective and selective methods, subsequent reaction with the carrier typically takes place using EDAC, which activates carboxyl groups in the protein for reaction with the linker. This EDAC activation can result in activation of the carboxyl group in the KDO subunit, leading to unwanted side reactions. The EDAC activation can also result in cross-linking of the carrier protein, because activated carboxyl groups in the protein can react with primary amine groups in the protein instead of in the linker.

Accordingly, there remains a need for further and better ways of preparing conjugates, particularly of the core domain from the lipopolysaccharide of Gram-negative bacteria.

DISCLOSURE OF THE INVENTION

The invention is based on conjugation methods that can be used in place of the conjugation methods of the prior art. These methods may be quicker to perform than the prior art methods, particularly those methods that involve reductive amination. The methods also do not require the use of EDAC, which avoids unwanted side reactions. In developing these methods, the inventors have found ways of purifying intermediate compounds that do not require the use of toxic compounds. Accordingly, the methods may be carried out more safely. The resultant conjugates may have different, preferably improved, immunological properties compared to the conjugates of the prior art.

The invention therefore provides alternative or improved methods for conjugating a polysaccharide to a carrier protein, and conjugates obtained or obtainable by these methods. The invention also provides intermediate compounds that are useful in the methods of the invention and methods for preparing these intermediate compounds.

First Aspect of the Invention

In a first aspect, the invention provides a process for preparing a conjugate of a polysaccharide and a carrier molecule, comprising the steps of: (a) coupling the polysaccharide to a linker, to form a polysaccharide-linker intermediate in which the free terminus of the linker is an ester group; and (b) reacting the ester group with a primary amine group in the carrier molecule, to form a polysaccharide-linker-carrier molecule conjugate in which the linker is coupled to the carrier molecule via an amide linkage. Unlike the conjugation processes used in ref. 1, 2 and 13, the process does not require activation of the carrier molecule with EDAC, thereby avoiding unwanted side reactions. The invention also provides the individual steps (a) and (b) of this process; the conjugate obtained or obtainable by this process; and the polysaccharide-linker intermediate obtained or obtainable by step (a) of this process.

Step (a) of the First Aspect of the Invention

In step (a) of this first aspect of the invention, the polysaccharide is coupled to a linker to form a polysaccharide-linker intermediate in which the free terminus of the linker is an ester group. The linker is therefore one in which at least one terminus is an ester group. The other terminus is selected so that it can react with the polysaccharide to form the polysaccharide-linker intermediate, as explained below.

In some embodiments of the invention, the coupling in step (a) takes place directly. In these embodiments, the polysaccharide is typically coupled to the linker using a primary amine group in the polysaccharide. In these embodiments, the linker typically has an ester group at both termini. This allows the coupling to take place by reacting one of the ester groups with the primary amine group in the polysaccharide by nucleophilic acyl substitution. The reaction results in a polysaccharide-linker intermediate in which the polysaccharide is coupled to the linker via an amide linkage. In these embodiments, the linker is therefore a bifunctional linker that provides a first ester group for reacting with the primary amine group in the polysaccharide and a second ester group for reacting with the primary amine group in the carrier molecule. For example, a bifunctional linker of the formula $X_1$-L-$X_2$ may be used, where $X_1$ is an ester group that can react with the primary amine group in the polysaccharide; $X_2$ is an ester group that can react with the primary amine group in the carrier molecule; and L is a linking moiety in the linker. Typical L groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$), particularly —$(CH_2)_4$—. Homobifunctional linkers of the formula X-L-X are particularly suitable, where the two X groups are the same as each other and are capable of reacting with both of the primary amine groups; and where L is a linking moiety in the linker. A typical X group is N-oxysuccinimide. L typically has formula -L'-$L^2$-L'-, where L' is carbonyl. Typical $L^2$ groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$), particularly —$(CH_2)_4$—. A typical linker is thus adipic acid N-hydroxysuccinimide diester (SIDEA), and the inventors have found this compound to be particularly suitable as the linker for the invention:

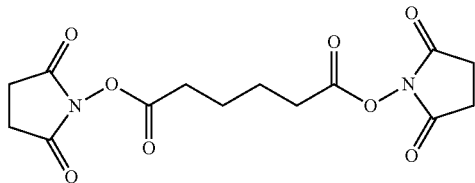 [SMILES: O=C(CCCCC(=O)ON1C(=O)CCC1=O)ON1C(=O)CCC1=O]

In alternative embodiments of the invention, the coupling in step (a) takes place indirectly, i.e. with an additional linker that is used to derivatise the polysaccharide prior to coupling to the linker.

In a first group of embodiments involving indirect coupling, the polysaccharide is coupled to the additional linker using a carbonyl group at the reducing terminus of the polysaccharide. This coupling comprises two steps: ($a_1$) reacting the carbonyl group with the additional linker; and ($a_2$) reacting the free terminus of the additional linker with the linker. In these embodiments, the additional linker typically has a primary amine group at both termini, thereby allowing step ($a_1$) to take place by reacting one of the primary amine groups with the carbonyl group in the polysaccharide by reductive amination. A primary amine group is used that is reactive with the carbonyl group in the polysaccharide. The inventors have found that a hydrazide (especially —C(=O)NHNH$_2$) or hydroxylamino (—ONH$_2$) group is suitable. The same primary amine group is typically present at both termini of the additional linker. Preferably, the reductive amination is carried out according to the process of the second aspect of the invention, which is described in detail below. The reaction results in a polysaccharide-additional linker intermediate in which the polysaccharide is coupled to the additional linker via a C—N linkage.

In a second group of embodiments involving indirect coupling, the polysaccharide is coupled to the additional linker using a different group in the polysaccharide, particularly a carboxyl group. This coupling comprises two steps: ($a_1$) reacting the group with the additional linker; and ($a_2$) reacting the free terminus of the additional linker with the linker. In these embodiments, the additional linker typically has a primary amine group at both termini, thereby allowing step ($a_1$) to take place by reacting one of the primary amine groups with the carboxyl group in the polysaccharide by EDAC activation. A primary amine group is used that is reactive with the EDAC-activated carboxyl group in the polysaccharide. A hydrazide (especially —C(=O)NHNH$_2$) group is suitable. The same primary amine group is typically present at both termini of the additional linker. The reaction results in a polysaccharide-additional linker intermediate in which the polysaccharide is coupled to the additional linker via an amide linkage.

These two groups of embodiments involving indirect coupling result in a polysaccharide-additional linker intermediate after step ($a_1$). The invention provides the polysaccharide-additional linker intermediate obtained or obtainable by these embodiments. The invention also provides individual steps ($a_1$) and ($a_2$) of these embodiments.

The free terminus of the additional linker is typically a primary amine group. Step ($a_2$) takes place using this primary amine group in the same way that the primary amine group is used in the embodiments involving direct coupling described above, with the same linker etc. This second step results in a polysaccharide-linker intermediate in which the polysaccharide is coupled to the linker via the additional linker, which additional linker is coupled to the linker via an amide linkage. The additional linker in these indirect embodiments is therefore typically a bifunctional linker that provides a first primary amine group for reacting with the carbonyl (or carboxyl) group in the polysaccharide and a second primary amine group for reacting with one of the ester groups in the linker. For example, a bifunctional linker of the formula $Y_1$-L-$Y_2$ may be used as the additional linker, where $Y_1$ comprises a primary amine group that can react with the carbonyl (or carboxyl) group in the polysaccharide; $Y_2$ comprises a primary amine group that can react with one of the ester groups in the linker; and L is a linking moiety in the additional linker. Typical L groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$), particularly —$(CH_2)_4$—. Homobifunctional linkers of the formula Y-L-Y are particularly suitable as the additional linker, where the two Y groups are the same as each other and are capable of reacting with both the carbonyl (or carboxyl) group and the ester group; and where L is a linking moiety in the additional linker. A typical Y group is a —NHNH$_2$ group. L typically has formula -L'-$L^2$-L'-, where L' is carbonyl. Typical $L^2$ groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$), particularly —$(CH_2)_4$—. A typical additional linker is thus adipic acid dihydrazide (ADH), and the inventors have found this compound to be particularly suitable as the additional linker for the invention. However, shorter additional linkers may be used, and the inventors have found that carbodihydrazine (CDH, i.e. Y-L-Y, wherein Y is —NHNH$_2$ and L is carbonyl) is also particularly suitable as the additional linker for the invention.

Step (b) of the First Aspect of the Invention

In step (b), the ester group at the free terminus of the linker in the polysaccharide-linker intermediate is reacted with a primary amine group in the carrier molecule. The reaction takes place by nucleophilic acyl substitution to form a polysaccharide-linker-carrier molecule conjugate in which the linker is coupled to the carrier molecule via an amide linkage.

Between step (a) and step (b), unreacted linker may be removed from the polysaccharide-linker intermediate. Preferably, this removal is carried out by the process of the third aspect of the invention, which is described in detail below.

Conjugates with a polysaccharide:protein ratio (w/w) of between 1:10 (i.e. excess protein) and 10:1 (i.e. excess polysaccharide) may be produced by the processes of the invention, depending on the molecular weights of the polysaccharide and the carrier molecule. For example, the conjugates may have excess saccharide, e.g. ratios of 10:1 to 1:1, with ratios greater than 1.5:1 being typical for O-antigen-core from S. Paratyphi coupled to CRM$_{197}$. Ratios between 8:1 and 1.5:1 are of particular interest, more specifically ratios between 6:1 and 2:1. In contrast, conjugates made by processes of the prior art tend to have excess protein, e.g. between 1:17 and 1:1.4 in reference 13. The inventors have found that ratios between 6:1 and 2:1, particularly between 3:1 and 4:1, are useful for conjugates containing O-antigen-core from S. Paratyphi and CRM$_{197}$. These conjugates can be manufactured efficiently and show similar immunogenicity to conjugates containing higher amounts of polysaccharide (e.g. ratios between 5:1 and 6:1). In terms of polysaccharide:protein ratio (mol/mol), the processes of the invention allow more than one polysaccharide chain to be conjugated to each carrier molecule, so ratios greater than 1:1 are typical.

Compositions may include a small amount of free carrier [14]. When a given carrier protein is present in both free and conjugated form in a composition of the invention, the unconjugated form is preferably no more than 5% of the total amount of the carrier protein in the composition as a whole, preferably present at less than 2% by weight, and more preferably present at less than 1% by weight.

After conjugation, free and conjugated polysaccharides can be separated. There are many suitable methods, including hydrophobic interaction chromatography (HIC), tangential flow filtration, size exclusion chromatography etc. [see also ref. 15 & 16, etc.].

The conjugate is preferably soluble in water and/or in a physiological buffer.

Second Aspect of the Invention

In a second aspect, the invention provides a process for the reductive amination of a carbonyl group at the reducing terminus of a polysaccharide, wherein the reductive amination is carried out at a pH between 4 and 5. The reductive amination may be carried out at a pH between 4.1 and 4.9, such as between 4.2 and 4.8, for example between 4.3 and 4.7, such as a pH between 4.4. and 4.6. The inventors have found that this relatively low pH allows the reaction to be carried out quickly (e.g. in 1 hour at 30° C.) compared to the 7 day reaction in ref. 13.

Preferably the reductive amination is carried out according to the process of the first aspect of the invention, specifically step (a$_1$) of the first group of embodiments involving indirect coupling described above. Accordingly, the reductive amination may comprise reacting the carbonyl group with the additional linker described above. The additional linker typically has a primary amine group at both termini, thereby allowing the reductive amination to take place by reacting one of the primary amine groups with the carbonyl group. A primary amine group is used that is reactive with the carbonyl group in the polysaccharide. The inventors have found that a hydrazide (especially —C(=O) NHNH$_2$) or hydroxylamino (—ONH$_2$) group is suitable. The same primary amine group is typically present at both termini of the additional linker. The reaction results in a polysaccharide-additional linker intermediate in which the polysaccharide is coupled to the additional linker via a C—N linkage. The invention also provides the polysaccharide-additional linker intermediate obtained or obtainable by this process.

The additional linker may in particular be a bifunctional linker of the formula Y$_1$-L-Y$_2$, where Y$_1$ comprises a primary amine group that can react with the carbonyl group in the polysaccharide; Y$_2$ comprises a second reactive group which can be linked to the carrier molecule, such as for example a primary amine group or a —SH group; and L is a linking moiety in the additional linker. Typical L groups are straight chain alkyls with 1 to 10 carbon atoms (e.g. C$_1$, C$_2$, C$_3$, C$_4$, C$_5$, C$_6$, C$_7$, C$_8$, C$_9$, C$_{10}$), particularly —(CH$_2$)$_4$—. Homobifunctional linkers of the formula Y-L-Y are particularly suitable as the additional linker, where the two Y groups are the same as each other and are capable of reacting with the carbonyl group; and where L is a linking moiety in the additional linker. A typical X group is a —NHNH$_2$ group. L typically has formula -L'-L$^2$-L'-, where L' is carbonyl. Typical L$^2$ groups are straight chain alkyls with 1 to 10 carbon atoms (e.g. C$_1$, C$_2$, C$_3$, C$_4$, C$_5$, C$_6$, C$_7$, C$_8$, C$_9$, C$_{10}$), particularly —(CH$_2$)$_4$—. A typical additional linker is thus adipic acid dihydrazide (ADH), and the inventors have found this compound to be particularly suitable as the additional linker for the invention. However, shorter additional linkers may be used, and the inventors have found that carbodihydrazine (CDH, i.e. Y-L-Y, wherein Y is —NHNH$_2$ and L is carbonyl) is also particularly suitable as the additional linker for the invention.

This process is particularly suitable when the polysaccharide is the O-antigen-core from a lipopolysaccharide, particularly from S. Paratyphi A. S. Typhimurium or S. Enteritidis.

Reductive amination is a standard technique in organic chemistry, and has been used extensively in the production of conjugates of capsular polysaccharides for vaccine use, including O-antigen-core [13]. In the second aspect of the invention, a carbonyl group in the polysaccharide reacts with a primary amine group, e.g. in the additional linker described above. This step also takes place in the process of the first aspect of the invention, specifically step (a$_1$) of the first group of embodiments involving indirect coupling described above. The reductive amination can conveniently be achieved by combining the polysaccharide with the primary amine group in the presence of an appropriate reducing agent (e.g. cyanoborohydrides, such as sodium cyanoborohydride NaBH$_3$CN; borane-pyridine; sodium triacetoxyborohydride; borohydride exchange resin; etc.). The skilled person would be capable of identifying suitable conditions for reductive amination. For example, the inventors have found that treatment of polysaccharide (O-antigen-core from S. Paratyphi, S. Typhimurium or S. Enteritidis) at 40 mg/ml in 100 mM sodium acetate at pH 4.5 with additional linker (ADH or CDH) at a 2:1 polysaccharide: additional linker ratio (w/w) and NaBH$_3$CN at a 2:1 polysaccharide:NaBH$_3$CN ratio is suitable. The reaction is typically left for 1 hour at 30° C.

Third Aspect of the Invention

In a third aspect, the invention provides a process for reducing contamination of a polysaccharide-linker intermediate with unreacted linker, comprising a step of precipitating unreacted linker under aqueous conditions at a pH of less than 5. This process does not require the use of toxic solvents such as dioxane or ethyl acetate. In particular, the process allows the decontamination to take place under aqueous conditions while avoiding polysaccharide-linker intermediate deactivation (e.g. by hydrolysis).

Preferably, the polysaccharide-linker intermediate is the intermediate obtained or obtainable by step (a) of the first aspect of the invention, described above. This process is particularly suitable when the linker is SIDEA. The polysaccharide may in particular be the O-antigen-core from a lipopolysaccharide, particularly from *S. Paratyphi* A, *S. Typhimurium* or *S. Enteritidis*.

Typically, the pH at which precipitation takes place is between 2 and 5. In embodiments of the invention the pH may be between 2-3, 3-4 or 4-5. Any suitable aqueous solution may be used to obtain this pH. For example, the inventors have found that addition of an aqueous buffer solution, e.g. aqueous citrate buffer, is suitable. The citrate buffer may for example be 100 mM sodium citrate at pH 3. The volume of added aqueous solution is selected to ensure that the unreacted linker is insoluble in the final mixture. For example, the inventors have found that a water content (vol/vol) of >60% (e.g. 61, 62, 63, 64, 65, 66, 67, 68, 69, 70% etc.) is suitable, particularly for the SIDEA linker. These conditions may be obtained, for example, by tripling the total volume of the reaction mixture with 100 mM sodium citrate solution at pH 3. The mixture is typically left for about 30 minutes. The precipitate is removed, e.g. by centrifugation.

The inventors have also found that an aqueous solution of hydrochloric acid (HCl) is suitable to reduce the pH. For example 2× volume of HCl 82.5 ppm is added to the reaction mixture to a concentration of HCl of 55 ppm in the final mixture, resulting in a pH of 2.3. The solution is mixed at 4° C. for 30 min and the solution recovered by centrifugation.

The polysaccharide-linker intermediate may be recovered from solution by precipitation with alcohol. In this way, the contamination of the polysaccharide-linker intermediate with unreacted linker is reduced, e.g. to less than 10% by the number of moles of unreacted linker relative to the number of moles of linker in the Intermediate.

The alcohol may in particular be ethanol, although other lower alcohols may be used (e.g. methanol, propan-1-ol, propan-2-ol, butan-1-ol, butan-2-ol, 2-methyl-propan-1-ol, 2-methyl-propan-2-ol, diols etc.). The ethanol is typically added to the solution containing the polysaccharide-linker intermediate to give a final ethanol concentration (vol/vol) of between 80% and 95%. The optimum final ethanol concentration may depend on the polysaccharide-linker intermediate. When the polysaccharide is the O-antigen-core from *S. Paratyphi* A, the inventors have found that a concentration of about 85% is suitable.

The ethanol may be added to the solution containing the polysaccharide-linker intermediate in pure form or may be added in a form diluted with a miscible solvent (e.g. water). The precipitated polysaccharide-linker intermediate is recovered, e.g. by centrifugation. It may be washed before further use.

In one embodiment the intermediate with the SIDEA linker is precipitated using 2-propanol (90% final concentration v/v) and the precipitate OAg-SIDEA is washed with absolute ethanol.

Preferably, the recovered polysaccharide-linker intermediate is then used in step (b) of the first aspect of the invention, described above. The process of this third aspect of the invention may in particular take place between steps (a) and (b) of the process of the first aspect of the invention.

The Polysaccharide

The invention involves a polysaccharide. Typically, the polysaccharide has a reducing terminus that is a KDO subunit. The KDO subunit comprises a carbonyl group. In some embodiments of the first aspect of the invention (specifically the first group of embodiments involving indirect coupling described above), the carbonyl group is used for coupling the polysaccharide to the linker in step (a) of the process. In the second aspect of the invention, the carbonyl group takes part in the reductive amination of the process. In both aspects, although it is typical for the polysaccharide to have a reducing terminus that is a KDO subunit, the skilled person will appreciate that other polysaccharides may be used that comprise a carbonyl group at their reducing termini. For example, the inventors have found that the capsular polysaccharide of *N. meningitidis* serogroup X may be used. Other bacterial capsular polysaccharides that may be suitable for use in the invention are described below. The KDO subunit also comprises a carboxyl group. In some embodiments of the first aspect of the invention (specifically within the second group of embodiments involving indirect coupling described above), the carboxyl group is used for coupling the polysaccharide to the linker in step (a) of the process. Again, the skilled person will appreciate that other polysaccharides may be used that comprise a carboxyl group. For example, bacterial capsular polysaccharides that may be suitable for use in the invention are described below In other embodiments of the first aspect of the invention (specifically the embodiments involving direct coupling described above), the polysaccharide is coupled to the linker in step (a) of the process using a primary amine group in the polysaccharide. In these processes it is not necessary for the polysaccharide to comprise a carbonyl group at its reducing terminus or a carboxyl group, although these groups will typically be present anyway (e.g. when the polysaccharide has a reducing terminus that is a KDO subunit). Again, the skilled person will appreciate that other polysaccharides may be used that comprise a primary amine group. For example, capsular polysaccharides that may be suitable for use in the invention are described below The polysaccharide may in particular comprise the core domain from the lipopolysaccharide of a Gram-negative bacterium. The core domain is a component of the lipopolysaccharide found in the outer membrane of the Gram negative bacterium. The lipopolysaccharide also comprises an O-antigen, which is linked via the core domain to a lipid A domain. The core domain has a terminal KDO subunit, which is linked to the lipid A domain in the native lipopolysaccharide. This KDO subunit may be the KDO subunit described above that may be at the reducing terminus of a polysaccharide used in the invention. The polysaccharide used in the invention may therefore comprise a core domain from a lipopolysaccharide. In preferred embodiments, this polysaccharide also comprises an O-antigen linked to the core domain (referred to herein as an O-antigen-core). The O-antigen-core is in particular the O-antigen and core domain from a specific lipopolysaccharide (i.e. the lipopolysaccharide without its lipid A domain). A typical process for the purification of these O-antigen-cores is based on the phenol-water method of Westphal and Jann, first described in the 1960s [ref. 17], followed by detoxification of the lipopolysaccharide with acetic acid or anhydrous hydrazine.

For example, this method was applied to *S. Typhimurium* in ref. 1; *S. Paratyphi* A in ref. 2; *S. dysentery* in ref. 13 and *E. coli* O157 in ref. 10. These methods involve sedimentation of the bacteria; inactivation of the culture by formalin fixation; hot phenol extraction of the lipopolysaccharide; and treatment of the extracted lipopolysaccharide with acetic acid (to remove the lipid A) or anhydrous hydrazine (to de-O-acylate the lipid A) prior to purification. These methods may also involve treatment of the disrupted cell mass or the extracted lipopolysaccharide with DNAse, RNAse and proteinase to reduce impurities.

For performing the reductive amination at the KDO carbonyl group described herein, lipid A should be removed leaving the KDO group free to react. For this purpose extraction and purification of polysaccharide can preferably be performed by acetic acid hydrolysis as described in for example references 1-2-10-13 and 18. However, the invention can be applied to any suitable O-antigen-core, including O-antigen-core obtained by different purification methods.

Polysaccharides comprising a core domain are preferred because they provide a KDO subunit for coupling the polysaccharide to the linker in step (a) of the first aspect of the invention. In particular, the KDO subunit comprises a carbonyl group for the first group of embodiments involving indirect coupling described above. The KDO subunit also contains a carboxyl group for the second group of embodiments involving indirect coupling described above. The polysaccharide also provides a KDO subunit for the reductive amination of the second aspect of the invention. In particular, the KDO subunit comprises a carbonyl group for the reductive amination described above. In those embodiments of the first aspect of the invention that involve coupling of the polysaccharide to the linker in step (a) of the process using a primary amine group in the polysaccharide, it is also useful for the polysaccharide to comprise a core domain from a lipopolysaccharide. This is because the core domain typically comprises a primary amine group (e.g. within a phosphoethanolamine group, particularly a pyrophosphoethanolamine group as in the *S. Paratyphi* A core domain). The use of such a polysaccharide with a core domain that contains a primary amine group is therefore preferred for these alternative embodiments of the first aspect of the invention. However, the phosphoethanolamine content may vary between core domains obtained from different bacteria or strains of the same bacterium. Accordingly, those embodiments of the first aspect of the invention that involve coupling of the polysaccharide to the linker in step (a) of the process using a KDO subunit are preferred. Of these embodiments, the processes involving reductive amination are particularly preferred because the resultant C—N linkage may be more stable than the linkage obtained via the phosphoethanolamine group.

Typically, the O-antigen and core domain is from the lipopolysaccharide of a *Salmonella* bacterium, e.g. from *Salmonella* serogroups A, B or D, and particularly from *Salmonella Paratyphi* A. The O-antigens of *Salmonella* serogroups A, B and D have been described and are thought to share a common backbone: →2-α-D-Manp-(1→4)-α-L-Rhap-(1→3)-α-D-Galp-(1→. The serogroup specificity of *Salmonella Paratyphi* A is conferred by an α-3,6-dideoxy-glucose (α-D-paratose) linked (1→3) to the mannose of the backbone. The α-L-rhamnose of the backbone is partially O-acetylated at C-3 (ref. 2, FIG. 1a). The α-D-paratose has also been reported to have various degrees of O-acetylation. The O-antigen from *S. Paratyphi* A is sometimes referred to as O:2. The published structure of the O-antigen and core domain from *S. Paratyphi* A is shown in FIG. 2, including the KDO subunit and primary amine group (within a pyrophosphoethanolamine group) in the core domain. The O-antigen in the invention may also be from *S. Typhimurium*. The published structure of the repeating unit of this O-antigen (sometimes referred to as O:4,5) is shown in FIG. 1b. The O-antigen may also be from *S. Enteriditis* (O:9, published structure of the repeating unit shown in FIG. 1c). Naturally-derived O-antigens may contain structural variations compared to the published structures for these O-antigens.

The O-antigen and core domain may also be from *Shigella* species, e.g. from *S. flexneri*. Other *Shigella* species that may provide the O-antigen and core domain used in the invention are *S. sonnei, S. dysenteriae* and *S. boydii* [ref. 19]. The O-antigen and core domain may also be from *E. coli*, e.g. *E. coli* O157. Other lipopolysaccharide-containing Gram-negative bacteria that may provide the O-antigen and core domain used in the invention are *Klebsiella pneumonia* [ref. 20], *Vibrio cholerae* [ref. 21], *Hoemophilus influenzae* and *Neisseria meningitidis* [ref. 22].

The polysaccharide may be chemically modified relative to the polysaccharide as found in nature. For example, the polysaccharide may be de-O-acetylated (partially or fully), but it is preferred for polysaccharides comprising O-antigen not to be de-O-acetylated. If it takes place, then de-acetylation may occur before, during or after other processing steps, but typically occurs before any coupling step. The effect of de-acetylation etc. can be assessed by routine assays. For example, the relevance of O-acetylation on *S. Paratyphi* A O-antigen is discussed in reference 2. The native O-antigen of *S. Paratyphi* A is said in this document to have about 80% O-acetylation. Conjugated de-O-acetylated O-antigen did not elicit anti-lipopolysaccharide antibodies with bactericidal activity. Accordingly, the *S. Paratyphi* A O-antigen used in the present invention may have between 0 and 100% O-acetylation, but it is preferred for the O-antigen to be O-acetylated. The level of O-acetylation may depend on the bacterial strain that provided the O-antigen. For example, the degree of O-acetylation of the *S. Paratyphi* A O-antigen may be 10-100%, 20-100%, 30-100%, 40-100%, 50-100%, 55-95%, 55-85%, 60-80% or 65-75%. Typically, the degree of O-acetylation of the *S. Paratyphi* A O-antigen is 55-85%, particularly 65-75%. However, higher degrees of O-acetylation, e.g. 70-100%, particularly 85-95% are also typical in some strains.

The degree of O-acetylation of the polysaccharide can be determined by any method known in the art, for example, by proton NMR (e.g. as described in reference 23), carbon NMR (e.g. as described in reference 2), the Hestrin method [24] or HPAEC-CD [25]. O-acetyl groups may be removed by hydrolysis, for example by treatment with a base such as anhydrous hydrazine [2]. To maintain high levels of O-acetylation on the polysaccharide, treatments that lead to hydrolysis of the O-acetyl groups are minimised, e.g. treatments at extremes of pH.

Other polysaccharides may be used in the invention. The skilled person would be capable of identifying suitable polysaccharides based on the polysaccharide comprising a reactive group used in the process of the invention (i.e. a carbonyl, carboxyl or primary amino group). In particular, bacterial capsular polysaccharides may be used in the invention. These bacterial capsular polysaccharides may for example be from *N. meningitidis*, particularly serogroups A, C, W135 and Y; *S. pneumoniae*, particularly from serotypes: 1, 2, 3, 4, 5, 6A, 6B, 7F, 8, 9N, 9V, 10A, 11A, 12F, 14, 15B, 17F, 18C, 19A, 19F, 20, 22F, 23F and 33F; *S. agalactiae*, particularly serotypes 1a, 1b, and III; *S. aureus*, particularly from *S. aureus* type 5 and type 8; *Haemophilus influenzae*

Type b; *Salmonella enterica* Typhi Vi; and *Clostridium difficile*. The invention may also use non-capsular bacterial polysaccharides. An exemplary non-capsular bacterial polysaccharide is the *S. pyogenes* GAS carbohydrate (also known as the GAS cell wall polysaccharide, or GASP). The invention may also use non-bacterial polysaccharides. For example, the invention may use glucans, e.g. from fungal cell walls. Representative glucans include laminarin and curdlan.

The polysaccharides may be used in the form of oligosaccharides. These are conveniently formed by fragmentation of purified polysaccharide (e.g. by hydrolysis), which will usually be followed by purification of the fragments of the desired size.

Polysaccharides can be purified by known techniques. The invention is not limited to polysaccharides purified from natural sources, however, and the polysaccharides may be obtained by other methods, such as total or partial synthesis.

The Carrier Molecule

The invention involves the use of carrier molecules, which are typically proteins. In general, covalent conjugation of saccharides to carriers enhances the immunogenicity of saccharides as it converts them from T-independent antigens to T-dependent antigens, thus allowing priming for immunological memory. Conjugation is particularly useful for paediatric vaccines [e.g. ref. 26] and is a well known technique [e.g. reviewed in ref. 27 to 35].

Preferred carrier proteins are bacterial toxins, such as diphtheria or tetanus toxins, or toxoids or mutants thereof. These are commonly used in conjugate vaccines. The $CRM_{197}$ diphtheria toxin mutant is particularly preferred [36].

Other suitable carrier proteins include the *Neisseria meningitidis* outer membrane protein complex [37], synthetic peptides [38,39], heat shock proteins [40,41], pertussis proteins [42,43], cytokines [44], lymphokines [44], hormones [44], growth factors [44], artificial proteins comprising multiple human $CD4^+$ T cell epitopes from various pathogen-derived antigens [45] such as N19 [46], protein D from *Haemophilus influenzae* [47-49], pneumolysin [50] or its non-toxic derivatives [51], pneumococcal surface protein PspA [52], iron-uptake proteins [53], toxin A or B from *Clostridium difficile* [54], recombinant *Pseudomonas aeruginosa* exoprotein A (rEPA) [55], etc.

It is possible to use mixtures of carrier proteins. A single carrier protein may carry multiple different polysaccharides [56].

Combinations of Conjugates and other Antigens

As well as providing individual conjugates as described above, the invention provides a composition comprising a conjugate of the invention and one or more further antigens. The composition is typically an immunogenic composition.

The further antigen is preferably capsular polysaccharide from *Salmonella Typhi* (Vi) or *Citrobacter* Vi. This capsular saccharide may be conjugated, e.g. to recombinant mutant *P. aeruginosa* exoprotein A (as in ref. 57) or more preferably to $CRM_{197}$ [36, 58, 59]. A preferred Vi-$CRM_{197}$ conjugate for use in the present invention is described in reference 60.

The further antigen(s) may comprise further conjugates, either prepared by a process of the invention or by a different process. For example, in one embodiment the present invention provides a composition comprising a conjugate of *S. Typhimurium* O-antigen-core and a conjugate of *S. Enteriditis* O-antigen-core, wherein at least one (more typically both) of the conjugates is prepared by a process of the invention. In another embodiments, the present invention provides a composition comprising a conjugate of *S. Para-typhi* A O-antigen-core, a conjugate of *S. Typhimurium* O-antigen-core and a conjugate of *S. Enteriditis* O-antigen-core, wherein at least one of the conjugates (e.g. two or more, typically all three) is prepared by a process of the invention.

In other embodiments, the one or more further antigen(s) are selected from the following
- a saccharide antigen from *Streptococcus pneumoniae* [e.g. ref. 61-63; chapters 22 & 23 of ref. 64].
- an antigen from hepatitis A virus, such as inactivated virus [e.g. 65, 66; chapter 15 of ref. 64].
- an antigen from hepatitis B virus, such as the surface and/or core antigens [e.g. 66,67; chapter 16 of ref. 64].
- an antigen from hepatitis C virus [e.g. 68].
- an antigen from *Bordetella pertussis*, such as pertussis holotoxin (PT) and filamentous hemagglutinin (FHA) from *B. pertussis*, optionally also in combination with pertactin and/or agglutinogens 2 and 3 [e.g. ref. 69 & 70; chapter 21 of ref. 64].
- a diphtheria antigen, such as a diphtheria toxoid [e.g. chapter 13 of ref. 64].
- a tetanus antigen, such as a tetanus toxoid [e.g. chapter 27 of ref. 64].
- a saccharide antigen from *Haemophilus influenzae* B [e.g. chapter 14 of ref. 64]
- an antigen from *N. gonorrhoeae*
- an antigen from *Chlamydia pneumoniae* [e.g. 71, 72, 73, 74, 75, 76, 77].
- an antigen from *Chlamydia trachomatis* [e.g. 78].
- an antigen from *Porphyromonas gingivalis* [e.g. 79].
- polio antigen(s) [e.g. 80, 81; chapter 24 of ref. 64] such as IPV.
- rabies antigen(s) [e.g. 82] such as lyophilised inactivated virus [e.g. 83, RabAvert™].
- measles, mumps and/or rubella antigens [e.g. chapters 19, 20 and 26 of ref. 64].
- influenza antigen(s) [e.g. chapters 17 & 18 of ref. 64], such as the haemagglutinin and/or neuraminidase surface proteins.
- an antigen from *Moraxella catarrhalis* [e.g. 84].
- an antigen from *Streptococcus pyogenes* (group A streptococcus) [e.g. 85, 86, 87].
- an antigen from *Streptococcus agalactiae* (group B streptococcus) [e.g. 88-90].
- an antigen from *S. epidermidis* [e.g. type I, II and/or III capsular polysaccharide obtainable from strains ATCC-31432, SE-360 and SE-10 as described in ref. 91, 92 and 93].

Where a saccharide or carbohydrate antigen is used, it is typically conjugated to a carrier in order to enhance immunogenicity. Conjugation of *H. influenzae* B and pneumococcal saccharide antigens is well known.

Toxic protein antigens may be detoxified where necessary (e.g. detoxification of pertussis toxin by chemical and/or genetic means [70]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. These combinations may further comprise an antigen from hepatitis B virus and/or a saccharide antigen from *H. influenzae* B, typically both.

Antigens in the composition will typically be present at a concentration of at least 1 µg/ml each. In general, the concentration of any given antigen will be sufficient to elicit an immune response against that antigen.

As an alternative to using proteins antigens in the composition of the invention, nucleic acid encoding the antigen may be used [e.g. ref. 94 to 102]. Protein components of the compositions of the invention may thus be replaced by nucleic acid (usually DNA e.g. in the form of a plasmid) that encodes the protein.

Pharmaceutical Compositions and Methods

The invention provides a pharmaceutical composition comprising (a) a conjugate of the invention and (b) a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [103], trehalose [104], lactose, and lipid aggregates (such as oil droplets or liposomes). Such carriers are well known to those of ordinary skill in the art. The compositions may also contain diluents, such as water, saline, glycerol, etc. Additionally, auxiliary substances, such as wetting or emulsifying agent, pH buffering substances, and the like, may be present. Sterile pyrogen-free, phosphate-buffered physiologic saline is a typical carrier. A thorough discussion of pharmaceutically acceptable excipients is available in reference 105.

Compositions of the invention may be in aqueous form (i.e. solutions or suspensions) or in a dried form (e.g. lyophilised). If a dried vaccine is used then it will be reconstituted into a liquid medium prior to injection. Lyophilisation of conjugate vaccines is known in the art e.g. the Menjugate™ product is presented in lyophilised form, whereas NeisVac-C™ and Meningitec™ are presented in aqueous form. To stabilise conjugates during lyophilisation, it may be typical to include a sugar alcohol (e.g. mannitol) or a disaccharide (e.g. sucrose or trehalose) e.g. at between 1 mg/ml and 30 mg/ml (e.g. about 25 mg/ml) in the composition.

Compositions may be presented in vials, or they may be presented in ready-filled syringes. The syringes may be supplied with or without needles. A syringe will include a single dose of the composition, whereas a vial may include a single dose or multiple doses.

Aqueous compositions of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is typically between 6 and 8, e.g. about 7. Stable pH may be maintained by the use of a buffer. If a composition comprises an aluminium hydroxide salt, it is typical to use a histidine buffer [106]. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Within each dose, the quantity of an individual saccharide antigen will generally be between 1-50 μg (measured as mass of saccharide) e.g. about 1 μg, about 2 μg, about 4 μg, about 5 μg, or about 10 μg.

The compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs. 107 & 108]. Success with nasal administration of pneumococcal saccharides [109,110], Hib saccharides [111], MenC saccharides [112], and mixtures of Hib and MenC saccharide conjugates [113] has been reported.

Compositions of the invention may include an antimicrobial, particularly when packaged in multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention will generally be administered in conjunction with other immunoregulatory agents. In particular, compositions will usually include one or more adjuvants. Such adjuvants include, but are not limited to:

A. Mineral-containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 117], or mixtures of different mineral compounds, with the compounds taking any suitable form (e.g. gel, crystalline, amorphous, etc.), and with adsorption being preferred. The mineral containing compositions may also be formulated as a particle of metal salt.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 cm$^{-1}$ and a strong shoulder at 3090-3100 cm$^{-1}$ [chapter 9 of ref. 117]. The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. at 200° C.) indicates the presence of structural hydroxyls [ch. 9 of ref. 117].

The PO$_4$/Al$^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with PO$_4$/Al molar ratio between 0.84 and 0.92, included at 0.6 mg Al$^{3+}$/ml. The aluminium phosphate will generally be particulate (e.g. plate-like morphology as seen in transmission electron micrographs). Typical diameters of the particles are in the range 0.5-20 µm (e.g. about 5-10 µm) after any antigen adsorption. Adsorptive capacities of between 0.7-1.5 mg protein per mg Al$^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

In one embodiment, an adjuvant component includes a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of Al$^{+++}$ in a composition for administration to a patient is preferably less than 10 mg/ml e.g. ≤5 mg/m, ≤4 mg/ml, ≤3 mg/ml, ≤2 mg/ml, ≤1 mg/ml, etc. A preferred range is between 0.3 and 1 mg/ml. A maximum of <0.85 mg/dose is preferred.

B. Oil Emulsions

Oil emulsion compositions suitable for use as adjuvants in the invention include squalene-water emulsions, such as MF59 [Chapter 10 of ref. 117; see also ref. 114] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various suitable oil-in-water emulsions are known, and they typically include at least one oil and at least one surfactant, with the oil(s) and surfactant(s) being biodegradable (metabolisable) and biocompatible. The oil droplets in the emulsion are generally less than 5 m in diameter, and advantageously the emulsion comprises oil droplets with a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene. Other preferred oils are the tocopherols (see below). Oil in water emulsions comprising sqlauene are particularly preferred. Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IG- EPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Preferred surfactants for including in the emulsion are Tween 80 (polyoxyethylene sorbitan monooleate), Span 85 (sorbitan trioleate), lecithin and Triton X-100. As mentioned above, detergents such as Tween 80 may contribute to the thermal stability seen in the examples below.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [114-116], as described in more detail in Chapter 10 of ref. 117 and chapter 12 of ref. 118. The MF59 emulsion advantageously includes citrate ions e.g. 10 mM sodium citrate buffer.
- An emulsion comprising squalene, an α-tocopherol, and polysorbate 80. These emulsions may have from 2 to 10% squalene, from 2 to 10% tocopherol and from 0.3 to 3% Tween 80, and the weight ratio of squalene:tocopherol is preferably ≤1 (e.g. 0.90) as this provides a more stable emulsion. Squalene and Tween 80 may be present volume ratio of about 5:2, or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.
- An emulsion of squalene, a tocopherol, and a Triton detergent (e.g. Triton X-100). The emulsion may also include a 3d-MPL (see below). The emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 µg/ml polysorbate 80, 110 µg/ml Triton X-100 and 100 µg/ml α-tocopherol succinate), and these concentrations should include any contribution of these components from antigens. The emulsion may also include squalene. The emulsion may also include a 3d-MPL (see below). The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [119] (0.05-1% Thr-MDP, 5% squalane, 2.5% Pluronic L121 and 0.2% polysorbate 80). It can also be used without the Thr-MDP, as in the "AF" adjuvant [120] (5% squalane, 1.25% Pluronic L121 and 0.2% polysorbate 80). Microfluidisation is preferred.
- An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactan (e.g. a sorbitan ester or mannide ester, such as sorbitan monoleate or 'Span 80'). The emulsion is preferably thermoreversible and/or has at least 90% of the oil droplets (by volume) with a size less than 200 nm [121]. The emulsion may also include one or more of: alditol; a cryoprotective agent (e.g. a sugar, such as dodecylmaltoside and/or sucrose); and/or an alkylpolyglycoside. Such emulsions may be lyophilized.
- An emulsion having from 0.5-50% of an oil, 0.1-10% of a phospholipid, and 0.05-5% of a non-ionic surfactant. As described in reference 122, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 123, produced by addition of aliphatic amine to desacylsaponin via the carboxyl group of glucuronic acid), dimethyidioctadecylammonium bromide and/or N,N-dioctadecyl-N, N-bis (2-hydroxyethyl)propanediamine.
- An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [124].
- An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [124].
- An emulsion in which a saponin (e.g. QuilA or QS21) and a sterol (e.g. a cholesterol) are associated as helical micelles [125].

Antigens and adjuvants in a composition will typically be in admixture at the time of delivery to a patient. The emulsions may be mixed with antigen during manufacture, or extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1.

C. Saponin Formulations [Chapter 22 of Ref. 117]

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaparilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17. QS18, QS21, QH-A, QH-B and QH-C. Preferably, the saponin is QS21. A method of production of QS21 is disclosed in ref. 126. Saponin formulations may also comprise a sterol, such as cholesterol [127].

Combinations of saponins and cholesterols can be used to form unique particles called immunostimulating complexs (ISCOMs; see chapter 23 of ref. 117; also refs. 128 & 129). ISCOMs typically also include a phospholipid such as phosphatidylethanolamine or phosphatidylcholine. Any known saponin can be used in ISCOMs. Preferably, the ISCOM includes one or more of QuilA, QHA & QHC. Optionally, the ISCOMS may be devoid of additional detergent [130].

A review of the development of saponin based adjuvants can be found in ref. 131 & 132.

D. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory olignucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 133. Such "small particles" of 3dMPL are small enough to be sterile filtered through a 0.22 µm membrane [133]. Other non-toxic LPS derivatives include monophosphoryl lipid A mimics, such as aminoalkyl glucosaminide phosphate derivatives e.g. RC-529 [134,135].

Lipid A derivatives include derivatives of lipid A from *Escherichia coli* such as OM-174. OM-174 is described for example in ref. 136 & 137.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 138, 139 and 140 disclose possible analog substitutions e.g. replacement of guanosine with 2'-deoxy-7-deazaguanosine. The adjuvant effect of CpG oligonucleotides is further discussed in ref. 141-146.

The CpG sequence may be directed to TLR9, such as the motif GTCGTT or TTCGTT [147]. The CpG sequence may be specific for inducing a Th1 immune response, such as a CpG-A ODN, or it may be more specific for inducing a B cell response, such a CpG-B ODN. CpG-A and CpG-B ODNs are discussed in ref. 148-150. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, ref. 151-153.

A particularly useful adjuvant based around immunostimulatory oligonucleotides is known as IC-31™ [154-156]. Thus an adjuvant used with the invention may comprise a mixture of (i) an oligonucleotide (e.g. between 15-40 nucleotides) including at least one (and preferably multiple) Cp1 motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 1). The polycationic polymer may be a peptide comprising 11-mer amino acid sequence KLKLLLLLKLK (SEQ ID NO: 2). This combination of SEQ ID NOs: 1 and 2 provides the IC-31™ adjuvant.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 157 and as parenteral adjuvants in ref. 158. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 159-166. A useful CT mutant is or CT-E29H [167]. Numerical reference for amino acid substitutions is preferably based on the alignments of the A and B subunits of ADP-ribosylating toxins set forth in ref. 168, specifically incorporated herein by reference in its entirety.

E. Human Immunomodulators

Human immunomodulators suitable for use as adjuvants in the invention include cytokines, such as interleukins (e.g. IL-1, IL-2, IL-4, IL-5, IL-6, IL-7, IL-12 [169], etc.) [170], interferons (e.g. interferon-γ), macrophage colony stimulating factor, and tumor necrosis factor. A preferred immunomodulator is IL-12.

F. Bioadhesives and Mucoadhesives

Bioadhesives and mucoadhesives may also be used as adjuvants in the Invention. Suitable bioadhesives include esterified hyaluronic acid microspheres [171] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [172].

G. Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g.

with SDS) or a positively-charged surface (e.g. with a cationic detergent, such as CTAB).

H. Liposomes (Chapters 13 & 14 of ref. 117)

Examples of liposome formulations suitable for use as adjuvants are described in ref. 173-175.

I. Imidazoquinolone Compounds.

Examples of imidazoquinolone compounds suitable for use adjuvants in the invention include Imiquamod and its homologues (e.g. "Resiquimod 3M"), described further in ref. 176 and 177.

The invention may also comprise combinations of aspects of one or more of the adjuvants identified above. For example, the following adjuvant compositions may be used in the invention: (1) a saponin and an oil-in-water emulsion [178]; (2) a saponin (e.g. QS21)+a non-toxic LPS derivative (e.g. 3dMPL) [179]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [180]; (5) combinations of 3dMPL with, for example, QS21 and/or oil-in-water emulsions [181]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 117.

An aluminium hydroxide adjuvant is useful, and antigens are generally adsorbed to this salt. Oil-in-water emulsions comprising squalene, with submicron oil droplets, are also preferred, particularly in the elderly. Useful adjuvant combinations include combinations of Th1 and Th2 adjuvants such as CpG & an aluminium salt, or resiquimod & an aluminium salt. A combination of an aluminium salt and 3dMPL may be used.

Methods of Treatment

The invention also provides a method for raising an immune response in a mammal, comprising administering a pharmaceutical composition of the invention to the mammal. The immune response is preferably protective and preferably involves antibodies. The method may raise a booster response.

The mammal is preferably a human. Where the vaccine is for prophylactic use, the human is preferably a child (e.g. a toddler or infant) or a teenager, where the vaccine is for therapeutic use, the human is preferably an adult. A vaccine intended for children may also be administered to adults e.g. to assess safety, dosage, immunogenicity, etc. The mammal may also be a farm animal, e.g. a pig or cow. Such veterinary uses are specifically envisaged. The bird is preferably livestock, particularly a turkey or other poultry.

The invention also provides a composition of the invention for use as a medicament. The medicament is preferably able to raise an immune response in a mammal (i.e. it is an immunogenic composition) and is more preferably a vaccine.

The invention also provides the use of a conjugate of the invention in the manufacture of a medicament for raising an immune response in a mammal.

These uses and methods are preferably for the prevention and/or treatment of a disease caused by a bacterium from which the polysaccharide is derived.

One way of checking efficacy of therapeutic treatment involves monitoring bacterial infection after administration of the composition of the invention. One way of checking efficacy of prophylactic treatment involves monitoring immune responses against the bacterial antigens after administration of the composition, e.g. using a serum bactericidal antibody assay.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 182-189, etc.

Where the invention concerns an "epitope", this epitope may be a B-cell epitope and/or a T-cell epitope. Such epitopes can be identified empirically (e.g. using PEPSCAN [190,191] or similar methods), or they can be predicted (e.g. using the Jameson-Wolf antigenic index [192], matrix-based approaches [193], MAPITOPE [194], TEPITOPE [195, 196], neural networks [197], OptiMer & EpiMer [198, 199], ADEPT [200], Tsites [201], hydrophilicity [202], antigenic index [203] or the methods disclosed in references 204-208, etc.). Epitopes are the parts of an antigen that are recognised by and bind to the antigen binding sites of antibodies or T-cell receptors, and they may also be referred to as "antigenic determinants".

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. The different steps can be performed at very different times by different people in different places (e.g. in different countries).

It will be appreciated that sugar rings can exist in open and closed form and that both forms are encompassed by the invention. Similarly, it will be appreciated that sugars can exist in pyranose and furanose forms and that both forms are also encompassed. Different anomeric forms of sugars are also encompassed. KDO may in particular undergo rearrangements, particularly under acidic conditions. These derivative forms of KDO are also encompassed by the invention. For example, when the invention involves a KDO subunit (e.g. in the reductive amination of the first and second aspects), the subunit may be in one or more of these derivative forms.

A primary amine group can be represented by formula $NH_2R$. The R group will typically be electron donating, and includes —NH, —O, $C_{1-8}$hydrocarbyl, particularly $C_{1-8}$alkyl, especially methyl. R is often —$CH_3$, —$C_2H_5$ or —$C_3H_7$. The hydrocarbyl may be substituted with one or more groups, such as: halogen (e.g. Cl, Br, F, I), trihalomethyl, —$NO_2$, —CN, —$N^+(C_{1-6}alkyl)_2O^-$, —$SO_3H$, —$SOC_{1-6}$alkyl, —$SO_2C_{1-6}$alkyl, —$SO_3C_{1-6}$alkyl, —OC(=O)$OC_{1-6}$alkyl, —C(=O)H, —C(=O)$C_{1-6}$alkyl, —OC(=O)$C_{1-6}$alkyl, —N($C_{1-6}$alkyl)$_2$, $C_{1-6}$alkyl, —N($C_{1-6}$alkyl)$_2$, —C(=O)N($C_{1-6}$alkyl)$_2$, —N($C_{1-6}$alkyl)C(=O)O($C_{1-6}$alkyl), —N($C_{1-6}$alkyl)C(=O)N($C_{1-6}$alkyl)$_2$, —$CO_2H$, —OC(=O)N($C_{1-6}$alkyl)$_2$, —N($C_{1-6}$alkyl)C(=O)$C_{1-6}$alkyl, —N($C_{1-6}$alkyl)C(=S)$C_{1-6}$alkyl, —N($C_{1-6}$alkyl)$SO_2$N($C_{1-6}$alkyl)$_2$, —$CO_2C_{1-6}$alkyl, —$SO_2$N($C_{1-6}$alkyl)$_2$, —C(=O)$NH_2$, —C(=S)N($C_{1-6}$alkyl)$_2$, —N($C_{1-6}$alkyl)$SO_2C_{1-6}$alkyl, —N($C_{1-6}$alkyl)C(=S)N($C_{1-6}$alkyl)$_2$, —NH—$C_{1-6}$alkyl, —S—$C_{1-6}$alkyl or —O—$C_{1-6}$alkyl. The term 'hydrocarbyl' includes linear, branched or cyclic monovalent groups consisting of carbon and hydrogen. Hydrocarbyl groups thus include alkyl, alkenyl and alkynyl groups, cycloalkyl (including polycycloalkyl), cycloalkenyl and aryl groups and combinations thereof, e.g. alkylcycloalkyl, alkylpolycycloalkyl, alkylaryl, alkenylaryl, cycloalkylaryl, cycloalkenylaryl, cycloalkylalkyl, polycycloalkylalkyl, arylalkyl, arylalkenyl, arylcycloalkyl and arylcycloalkenyl groups. Typical hydrocarbyl are $C_{1-14}$ hydrocarbyl, more particularly $C_{1-8}$ hydrocarbyl. In the additional linker used in the invention, the primary amine group is typically part of a hydrazide (especially —C(=O)$NHNH_2$) group.

An ester group can be represented by formula —C(=O)OR. The R group will typically be electron donating, and includes $C_{1-8}$hydrocarbyl, particularly $C_{1-8}$alkyl, especially methyl. R is often —$CH_3$, —$C_2H_5$ or —$C_3H_7$. The hydrocarbyl may be substituted with one or more groups, such as: halogen (e.g. Cl, Br, F, I), trihalomethyl, —$NO_2$, —CN, —$N^+(C_{1-6}alkyl)_2O^-$, —$SO^3H$, —$SOC_{1-6}$alkyl, —$SO_2C_{1-6}$alkyl, —$SO_3C_{1-6}$alkyl, —OC(=O)$OC_{1-6}$alkyl, —C(=O)H, —C(=O)$C_{1-6}$alkyl, —OC(=O)$C_{1-6}$alkyl, —N($C_{1-6}$alkyl)$_2$, —$C_{1-6}$alkyl, —N($C_{1-6}$alkyl)$_2$, —C(=O)N($C_{1-6}$alkyl)$_2$, —N($C_{1-6}$alkyl)C(=O)O($C_{1-6}$alkyl), —N($C_{1-6}$alkyl)C(=O)N($C_{1-6}$alkyl)$_2$, —$CO_2H$, —OC(=O)N($C_{1-6}$alkyl)$_2$, —N($C_{1-6}$alkyl)C(=O)$C_{1-6}$alkyl, —N($C_{1-6}$alkyl)C(=S)$C_{1-6}$alkyl, —N($C_{1-6}$alkyl)$SO_2$N($C_{1-6}$alkyl)$_2$, —$CO_2C_{1-6}$alkyl, —$SO_2$N($C_{1-6}$alkyl)$_2$, —C(=O)$NH_2$, —C(=S)N($C_{1-6}$alkyl)$_2$, —N($C_{1-6}$alkyl)$SO_2C_{1-6}$alkyl, —N($C_{1-6}$alkyl)C(=S)N($C_{1-6}$alkyl)$_2$, —NH—$C_{1-6}$alkyl, —S—$C_{1-6}$alkyl or —O—$C_{1-6}$alkyl. The term 'hydrocarbyl' includes linear, branched or cyclic monovalent groups consisting of carbon and hydrogen. Hydrocarbyl groups thus include alkyl, alkenyl and alkynyl groups, cycloalkyl (including polycycloalkyl), cycloalkenyl and aryl groups and combinations thereof, e.g. alkylcycloalkyl, alkylpolycycloalkyl, alkylaryl, alkenylaryl, cycloalkylaryl, cycloalkenylaryl, cycloalkylalkyl, polycycloalkylalkyl, arylalkyl, arylalkenyl, arylcycloalkyl and arylcycloalkenyl groups. Typical hydrocarbyl are $C_{1-14}$ hydrocarbyl, more particularly $C_{1-8}$ hydrocarbyl. In the linker used in the invention, the ester group is typically a N-hydroxysuccinimide ester group.

BRIEF DESCRIPTION OF DRAWINGS

(FIG. 1B) *Salmonella Typhimurium*; and (FIG. 1C) *Salmonella Enteritidis*.

MODES FOR CARRYING OUT THE INVENTION

Summary of Conjugate Production

Figure 1A:
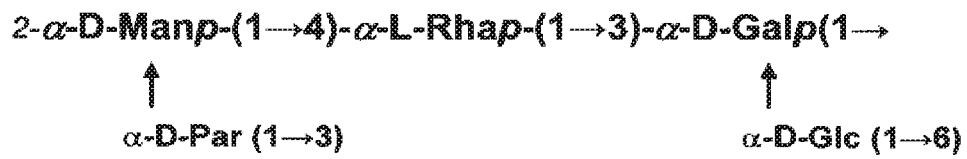
FIGS. 1A-C illustrate published structures of the repeating units of the O-antigens from (FIG. 1A) *Salmonella Paratyphi* A.
Figure 1B:
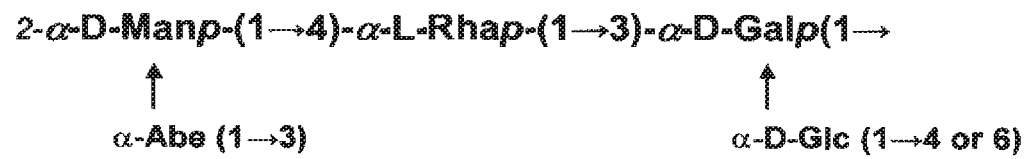
Figure 1C:
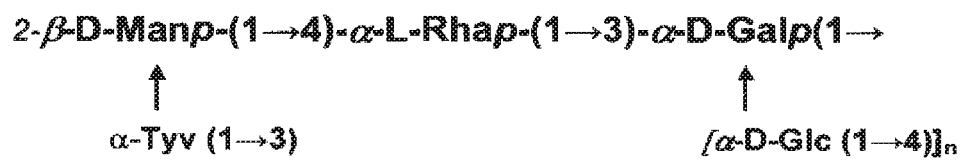
Figure 2:
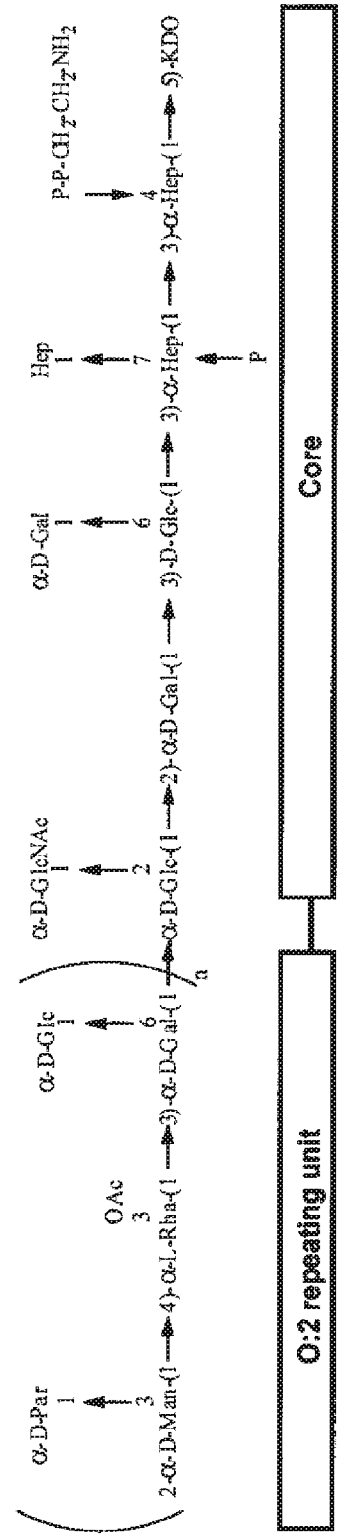
FIG. 2 illustrates the structure of the *Salmonella Paratyphi* A O-antigen repeating unit and core domain.

Different methods were compared for conjugating the O-antigen-core from *S. Paratyphi* to $CRM_{197}$. In particular, conjugates obtained by activating the O:2 chain randomly, or specifically through the terminal KDO subunit, were compared. Theoretically, activation of only the KDO would not modify the structure of the repeating saccharides and would therefore result in a better defined and easier to characterize conjugate.

Two methods were based on prior art methods. In the first of these methods, the O-antigen was randomly activated with ADH using CDAP and then conjugated to $CRM_{197}$ using EDAC. In the second method, the core region of the O-antigen was activated with ADH (using the COOH group of KDO by EDAC) and then conjugated to $CRM_{197}$ using EDAC.

Alternative methods were also tested. A first method involved KOO activation with ADH through the ketone group by reductive amination, followed by activation with SIDEA, and then conjugation with $CRM_{197}$. A second method substituted the ADH with CDH. A third method involved activation of O-antigen with SIDEA (without activation of KDO with ADH) using the pyrophosphoethanolamine group on the core region.

Conjugation of O-antigen-core to $CRM_{197}$ (Comparative) Method A: Random Activation of the O-antigen-core Chain with ADH by CDAP and Conjugation with $CRM_{197}$ by EDAC This conjugate was synthesized according to ref. 2, as described in detail below.

O-antigen-core derivatisation with ADH through CDAP. 30 µl of CDAP (100 mg/mL in acetonitrile) was added per ml of 10 mg/ml O-antigen-core in 150 mM NaCl at room temperature. The pH was maintained at 5.8 to 6.0 for 30 seconds, then 0.2 M TEA was added to increase the pH to 7.0 and the solution mixed at room temperature for 2 minutes. 1 ml of 0.8 M ADH in 0.5 M NaHC03 was then added per 10 mg of O-antigen-core. The reaction was carried out for 2 hours at room temperature, and pH maintained at 8.0 to 8.5 with 0.1 N NaOH. The reaction mixture was then desalted using a G-25 column against water and the product, designated as "OAg-(CDAP)ADH", characterized.

Conjugation of OAg-(CDAP)ADH with $CRM_{197}$. The OAg-(CDAP)ADH was dissolved in 100 mM MES at pH 5.8. An equal weight of protein was added to give an O-antigen-core:$CRM_{197}$ ratio of 1:1 by weight, with an O-antigen-core concentration of 5 mg/ml. The reaction mixture was placed on ice and EDAC added to a final concentration of 50 mM. The reaction was mixed on ice for a further 4 h. The resulting conjugate was designated "OAg-(CDAP)ADH-$CRM_{197}$".

(Comparative) Method B: Activation of Terminal KDO with ADH by EDAC and Conjugation with $CRM_{197}$ by EDAC This conjugate was synthesized according to ref. 9.

O-antigen-core derivatization with ADH at KDO through EDAC. The O-antigen-core was solubilized at 3 mg/ml in 100 mM MES at pH 5.8. ADH was then added at a w/w ratio ADH:O-antigen-core of 1.36, followed by EDAC to a final concentration of 3.7 mM. The reaction was mixed at room temperature for 4 hours. The reaction mixture was then desalted using a G-25 column against water and the product, designated as "OAg-(EDAC)ADH", characterized.

Conjugation of OAg-(EDAC)ADH with $CRM_{197}$. The conjugate was prepared according to the method described in Method A above for OAg-(CDAP)ADH. The conjugate was designated as "OAg-(EDAC)ADH-$CRM_{197}$".

Methods C and D: Activation of the Terminal KDO with ADH (Method C) or CDH (Method D) by Reductive Amination and Conjugation with $CRM_{197}$ via SIDEA Linker O-antigen-core derivatization with ADH or CDH at KDO by reductive amination. After testing different conditions, an optimized protocol for the O-antigen-core derivatization was identified. O-antigen-core was solubilized at 40 mg/ml in 100 mM AcONa at pH 4.5. Either ADH or CDH was added at a w/w ratio of 1:2 with respect to the O-antigen-core. $NaBH_3CN$ was then added at a w/w ratio of 1:2 with respect to the O-antigen-core. The solution was mixed at 30° C. for 1 hour. The reaction mixture was then desalted using a G-25 column against water and the product, designated as "OAg-ADH" or "OAg-CDH" characterized.

OAg-ADH and OAg-CDH derivatization with SIDEA. Either OAg-ADH or OAg-CDH was dissolved in 1:9 (vol/vol) water/DMSO to a final O-antigen-core concentration of 50 mg/ml. Once the polysaccharide was in solution, TEA was added to give a molar ratio of TEA/total $NH_2$ groups of 5 and then SIDEA to give a molar ratio of SIDEA/total $NH_2$ groups of 12. The solution was mixed at room temperature for 3 hours. In preliminary attempts to purify the SIDEA-derivatised O-antigen-core, the O-antigen-core was precipitated by addition of AcOEt or dioxane (90% volume in the resulting solution) and washing the pellet times with the same organic solvent (ten times using ⅓ of the volume added for the precipitation) in order to remove unreacted SIDEA. This process was then adapted to avoid the use of toxic AcOEt and dioxane reagents. A volume of 100 mM sodium citrate at pH 3 equal to two times the volume of the SIDEA-derivatised O-antigen-core reaction mixture was added and mixed at 4° C. for 30 min. Unreacted SIDEA was precipitated by the low pH and separated by centrifugation. The SIDEA-derivatised O-antigen-core was then recovered from the supernatant by precipitation with absolute ethanol (80% volume in the resulting solution). The pellet was washed with ethanol twice (using ⅓ of the volume added for the precipitation) and dried. The product, designated as "OAg-ADH-SIDEA" or "OAg-CDH-SIDEA" was characterized.

Conjugation of OAg-ADH-SIDEA and OAg-CDH-SIDEA with $CRM_{197}$. The OAg-ADH-SIDEA or OAg-CDH-SIDEA was solubilized in $NaH_2PO_4$ buffer at pH 7.2 and $CRM_{197}$ added to a final protein concentration of 20 mg/ml, final buffer capacity of 100 mM and molar ratio of active ester groups to $CRM_{197}$ of 30 to 1. The reaction was mixed at room temperature for 2 hours.

Method E: Direct Conjugation with $CRM_{197}$ via SIDEA Linker

The reaction conditions used in the above "OAg-ADH and OAg-CDH derivatization with SIDEA" was also applied to native O-antigen-core (i.e. O-antigen-core that had not previously been derivatized with ADH or CDH). The resulting product was designated as as "OAg-SIDEA". The OAg-SIDEA was then conjugated to $CRM_{197}$ by the reaction conditions used in the above "Conjugation of OAg-ADH-SIDEA and OAg-CDH-SIDEA with $CRM_{197}$".

Purification of the O-antigen-core Conjugates

Figure 3:
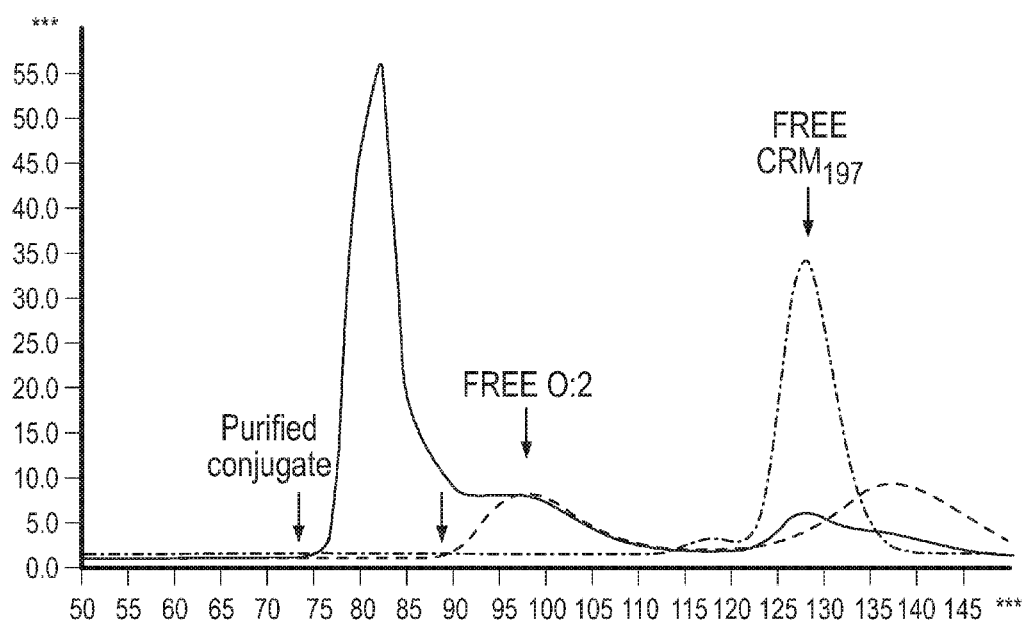
FIG. 3 shows the separation of O:2-$CRM_{197}$ from unconjugated components by Sephacryl S300HR.

Conjugates made according to methods A-E above were purified by size exclusion chromatography on a 1.6 cm×90 cm S-300 HR column eluted at 0.5 ml/min in 50 mM $NaH_2PO_4$, 0.15 M NaCl at pH 7.2. Different pools were collected according to free O-antigen-core and free $CRM_{197}$ profiles on the same column in the same eluting conditions (FIG. 3). The first pool at high molecular weight (corresponding to the purified conjugate) did not contain free saccharide or free protein.

Analysis of Conjugates

The conjugates were analysed by SDS-PAGE and showed an expected high molecular weight population smear compared to free $CRM_{197}$. The conjugates were separated from free O:2 and $CRM_{197}$ by Sephacryl S300HR size exclusion (1.6×90 cm column; 50 mM $NaH_2PO_4$, 150 mM NaCl pH 7.2; 0.5 mL/min flow). Results are shown in FIG. 3. Purified conjugates were then characterized by the phenol sulfuric assay of ref. 209 (total sugar), microBCA (total protein), HPAEC-PAD (sugar composition) and HPLC-SEC (size determination. Kd). Results are shown in Table 1 below.

TABLE 1

| Conjugate | Total sugar, μg/mL | Presence of free O:2 | Protein μg/mL | Wt/wt ratio O:2/CRM$_{197}$ | Kd (HPLC-SEC) |
|---|---|---|---|---|---|
| O:2 | | yes | | | 0.549 |
| CRM$_{197}$ | | | | | 0.690 |
| O:2-(CDAP)ADH-CRM$_{197}$ pool 1 | 32.88 | no | 62.98 | 0.52 | 0.439 |
| O:2-(CDAP)ADH-CRM$_{197}$ pool 2 | 101.09 | yes | 60.44 | 1.67 | 0.534 |
| O:2-CDH-SIDEA-CRM$_{197}$ Lot A | 82.82 | no | 36.67 | 2.26 | 0.403 |
| O:2-CDH-SIDEA-CRM$_{197}$ Lot B | 167.61 | no | 38.19 | 4.39 | 2 peaks 0.128 0.413 |
| O:2-ADH-SIDEA-CRM$_{197}$ Lot A | 51.54 | no | 29.56 | 1.74 | 2 peaks 0.115 0.388 |
| O:2-ADH-SIDEA-CRM$_{197}$ Lot B | 215.13 | no | 50.89 | 4.23 | 2 peaks 0.118 0.421 |
| O:2-(EDAC)ADH-CRM$_{197}$ | 50.19 | yes | 31.31 | 1.60 | 0.52 |
| O:2-SIDEA-CRM$_{197}$, pool 1 | 108.57 | no | 52.79 | 2.06 | 0.376 |
| O:2-SIDEA-CRM$_{197}$, pool 2 | 185.31 | yes | 68.18 | 2.72 | 0.457 |

Immunogenicity Studies

An ELISA immunoassay was used to detect anti-O:2 antibodies elicited by O:2-CRM$_{197}$ immunized mice. For the assay, MaxiSorp microtiter plates were coated with 15 μg/mL O:2 in a carbonate coating buffer (pH 9.6) overnight at 4° C.

The O:2-CRM$_{197}$ conjugates were compared to unconjugated O:2 antigen. Briefly, groups of female CDI mice (8 per group at 5 weeks of age) were injected subcutaneously with 200 μL of conjugates as set out in Table 2. Mice received immunizations on days 0, 14 and 28. Sera were collected from the mice during the course of the study and tested by the ELISA assay.

TABLE 2

| Group | Vaccine | O:2 antigen dose, μg |
|---|---|---|
| 1 | O:2-(CDAP)ADH-CRM$_{197}$, pool 1 | 1 |
| 2 | | 8 |
| 3 | O:2-(CDAP)ADH-CRM$_{197}$, pool 2 | 1 |
| 4 | | 8 |
| 5 | O:2-CDH-SIDEA-CRM$_{197}$ | 1 |
| 6 | | 8 |
| 7 | O:2-ADH-SIDEA-CRM$_{197}$ | 1 |
| 8 | | 8 |
| 9 | O:2-(EDAC)ADH-CRM$_{197}$ | 1 |
| 10 | | 8 |
| 11 | Unconjugated O:2 antigen | 8 |

Figure 4:
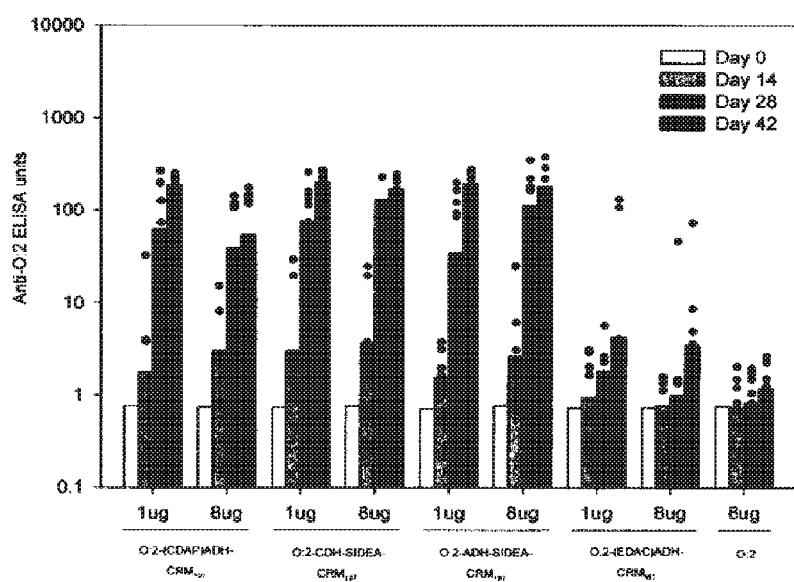
FIG. 4 shows the immunogenicity of different O:2-$CRM_{197}$ conjugates, as measured by an ELISA immunoassay for anti-O:2 antibodies.

ELISA results through day 42 of the study showed that all the conjugates, except O:2-(EDAC)ADH-CRM$_{197}$ were able to elicit high serum levels of anti-O:2 IgG antibodies in mice when delivered at the 1 μg dose (FIG. 4). Increases in antibody were observed following the second vaccination with conjugate, whereas repeated immunization with 8 μg of unconjugated O:2-antigen did not result in specific IgG antibodies. Delivery of 8 μg doses was no better than 1 μg doses at generating a humoral immune response in mice (FIG. 4).

Serum Bactericidal Activity

Figure 9:
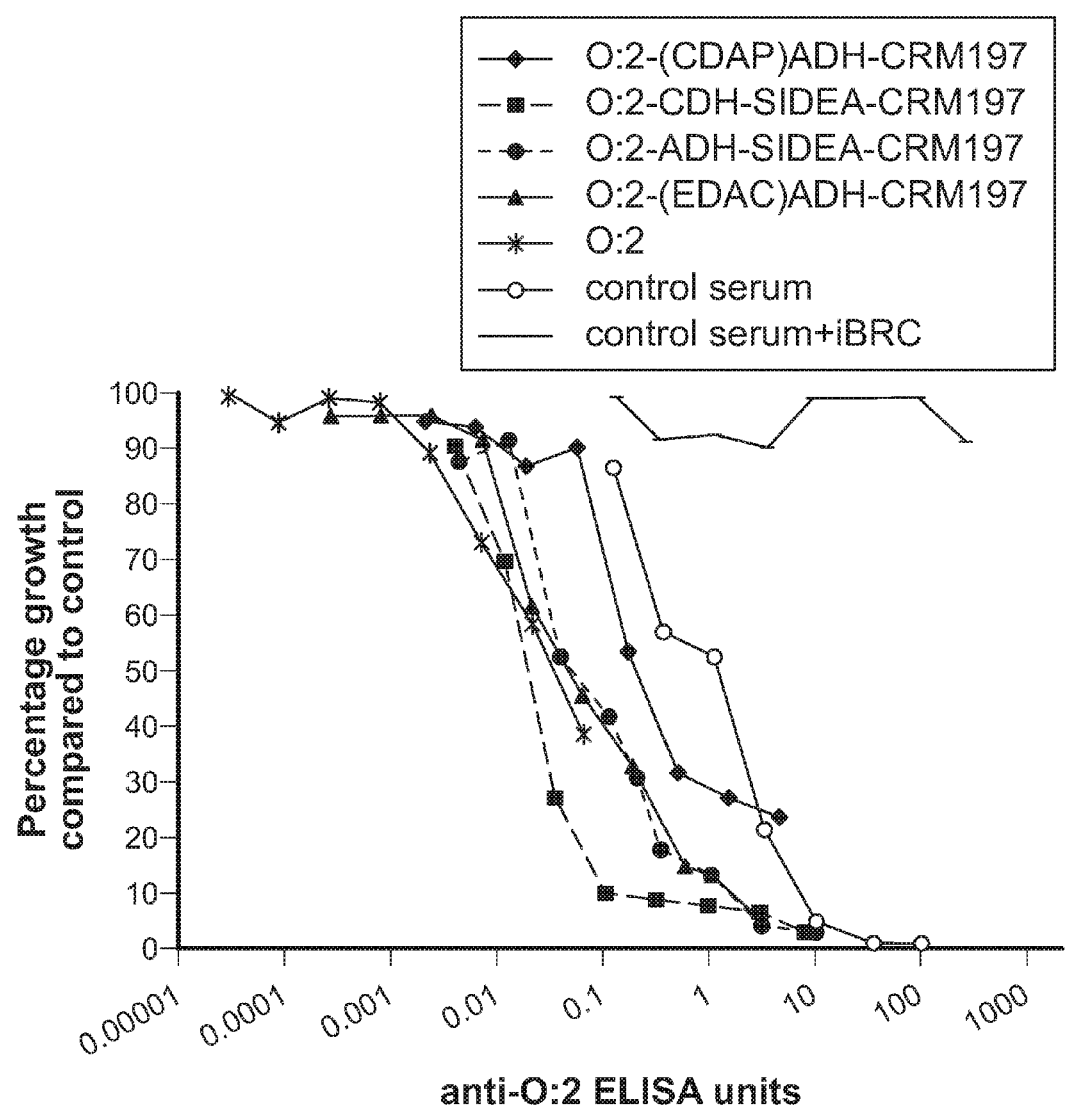
FIG. 9 shows the result of Serum Bactericidal Activity (SBA) assays performed using day 42 pooled sera from mice immunized with 8 ug of conjugated or unconjugated O:2 and *S. Paratyphi* A strain. Data are presented as percentage of CFU recovered in test sera with active BRC (and in control serum with inactive BRC) compared with CFU present in negative control, per anti-O:2 ELISA antibody unit of each serum pool.

Serum Bactericidal Activity (SBA) assays were performed using day 42 pooled sera from mice immunized with 8 ug of conjugated or unconjugated O:2 and S. Paratyphi A (see Table 2). The result is shown in FIG. 9. Inhibition of S. Paratyphi A growth in vitro correlated with increasing anti-O:2 ELISA units present in the sera pools. The strongest growth inhibition was observed with those conjugates produced using a selective chemistry; both SIDEA conjugates and O:2-(EDAC)ADH-CRM197 resulted in increased inhibition compared to O:2-(CDAP)ADH-CRM197, whose O:2 was randomly modified prior to conjugation. Even unconjugated O:2, although far from reaching high levels of bacterial growth inhibition due to the lower amount of antibody present in the sera, presented an inhibition profile similar to the conjugates prepared with unmodified O:2 chains. No bacterial growth inhibition was detected using control serum in the presence of iBRC (the same sera in the presence of active BRC is shown as control), indicating a role for complement mediated killing.

Larger-scale Processing

Figure 5:
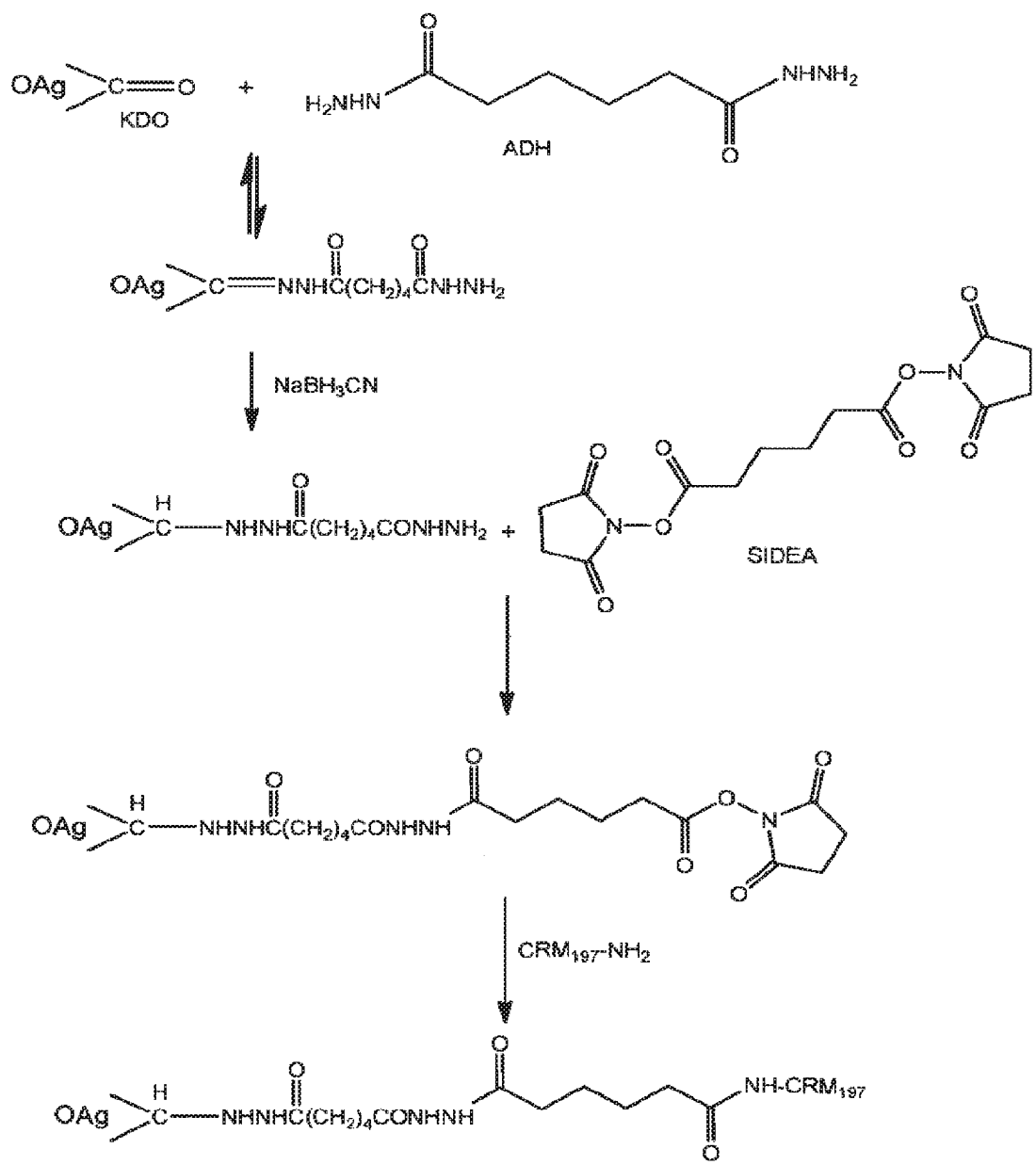
FIG. 5 is a schematic of a conjugation method of the invention applied to O-antigen-core.

Based on the immunogenicity study and ease of conjugate characterization, the conjugation method based on O:2-activation with ADH and then SIDEA and reaction with CRM$_{197}$ (method C, FIG. 5) was selected for further development. Conjugates made by this method were more immunogenic than conjugates made by the method B, for example. Although conjugates made by method A gave comparable ELISA titers (FIG. 4), they resulted in considerably lower Serum Bactericidal Activity (see Example and FIG. 9). Furthermore these conjugates had a cross-linked structure, with multiple possible points of linkage on the polysaccharide chain to one or more protein molecules, a with disadvantages in terms of reproducibility and characterization of the product. In contrast, the conjugates of method C contain more polysaccharide chains per protein molecule, with only one point of linkage on the polysaccharide chain. The remainder of the polysaccharide chain is left unchanged. Derivatization of the O-antigen-core through CDAP (method A) can result in crosslinking of the sugar chains and the overall conjugation method was more complicated. The use of EDAC in methods A and B can also result in cross-linking of the protein.

Figure 6:
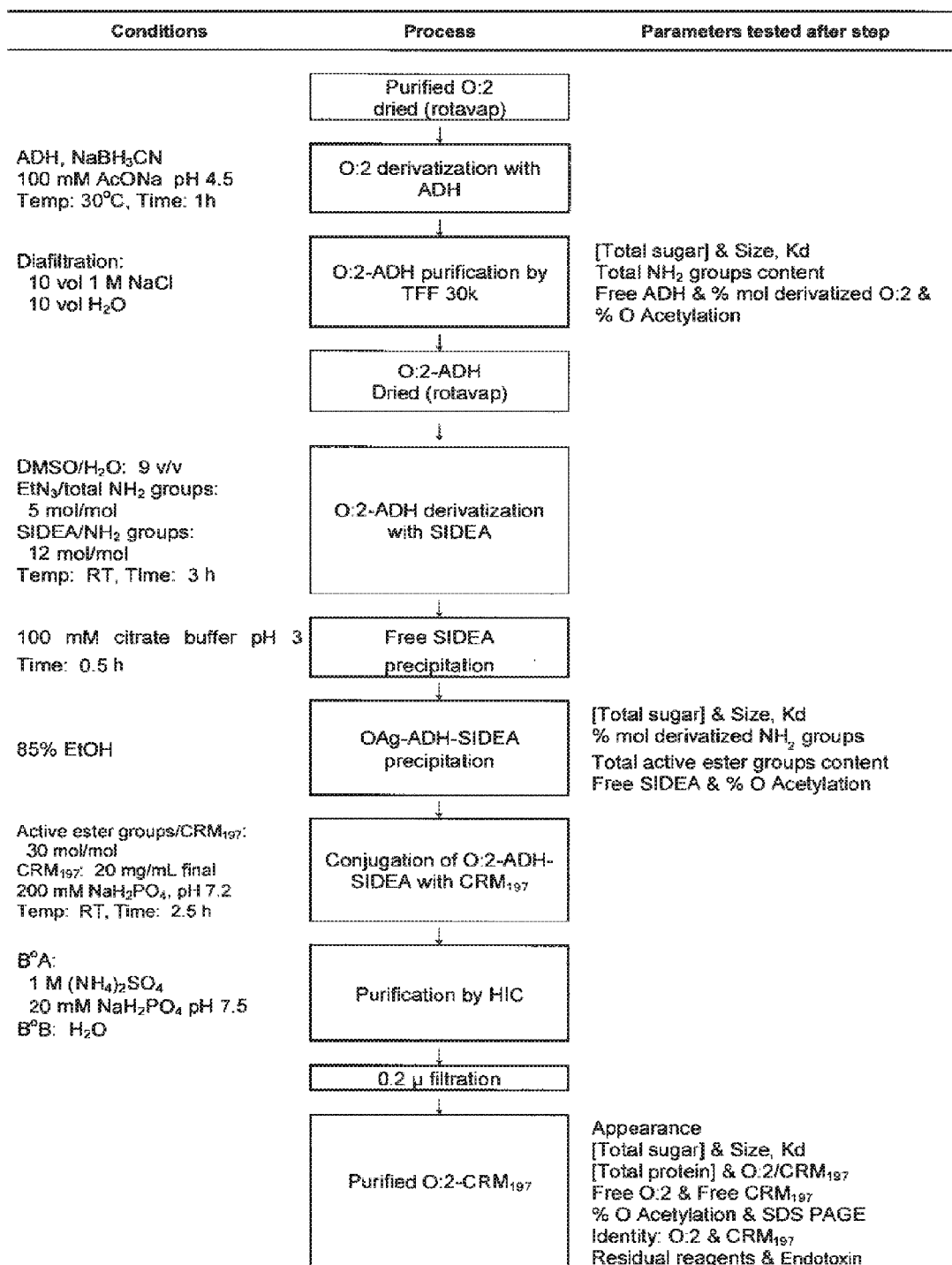
FIG. 6 illustrates a large scale method for the conjugation of O-antigen from *Salmonella Paratyphi* A to $CRM_{197}$.

A scaled-up process was developed for method C for the production of greater amounts of conjugate (FIG. 6). In particular, the step of O:2 reductive amination with ADH was optimized to reduce the reaction time to 1 hour (instead of 7-14 days as previous reported for this kind of reaction [13]) with good % of O:2 activation (>65%). This step was scaled to 300 mg of O:2 and repeated several times with reproducible results in terms of yield and derivatisation degree. Recovery was >75% after tangential flow filtration, with >70% of O-antigen-core activation (calculated as molar ratio of linked ADH groups per GlcNAc groups on the O-antigen-core) and good purity (ratio of free ADH/linked ADH<1%). The stability of the O:2-ADH intermediate in aqueous solution at 4° C. was verified to be >1 month. The inventors envisage replacing the drying step by O:2-ADH precipitation in 85% ethanol.

The reaction of O:2-ADH with SIDEA was optimized to avoid the use of AcOEt during O:2-ADH-SIDEA purification. Removal of free SIDEA by precipitation at pH 4-5 and then precipitation of O:2-ADH-SIDEA in 85% EtOH showed better precipitate formation that was easier to wash compared with AcOEt. Recoveries >85% were obtained working on a 100 mg scale with activated $NH_2$ groups >80%.

The inventors have found that in addition to O:2 from *S. Paratyphi* A the conjugation method based on O-antigen-core activation with ADH and then SIDEA and reaction with $CRM_{197}$ (method C, FIG. 5), works equally well for O-antigen-core from *S. Typhimurium* and O-antigen-core from *S. Enteritidis*.

Conjugation of MenX Capsular Polysaccharide to $CRM_{197}$

Figure 7:
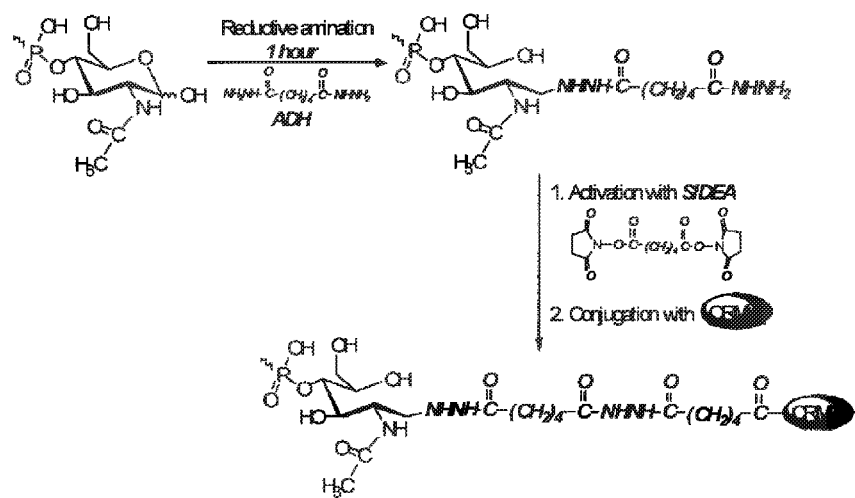
FIG. 7 is a schematic of a conjugation method of the invention applied to the capsular polysaccharide from *N. meningitidis* serogroup X.
Figure 8:
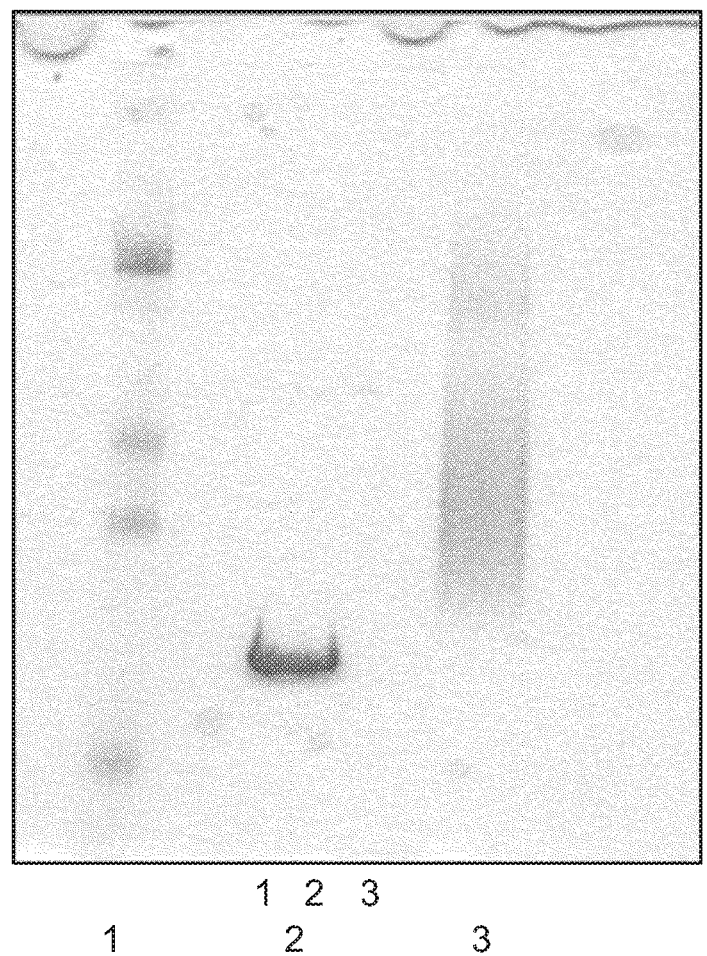
FIG. 8 shows an SDS-PAGE analysis of conjugates of capsular polysaccharide from *N. meningitidis* serogroup X and $CRM_{197}$.

Method C was also applied to the conjugation of capsular polysaccharide from *N. meningitidis* serogroup X (FIG. 7), resulting in conjugate formation with no free protein in the reaction mixture (FIG. 8).

It will be understood that the invention has been described by way of example only and modifications may be made whilst remaining within the scope and spirit of the invention.

Effect of pH and Temperature on the Reductive Amination of *S. Paratyphi* A O-antigen-core with ADH as Linker Experiments summarized in Table 3 were performed working with *S. Paratyphi* A O-antigen-core. The effect of different pH and different temperatures was evaluated. The best activation was obtained at lower pH and was temperature independent. Reactions were performed in 100 mM buffer, with O-antigen-core concentration of 20 mg/mL and a ratio of ADH to O-antigen-core and $NaBH_3CN$ to O-antigen-core both of 1.2 to 1 (w/w). ADH and $NaBH_3CN$ were added at the same time and solutions were mixed for 1 hour.

TABLE 3

Reductive amination of O:2-KDO with ADH is pH dependent and temperature independent.

| Buffer | Temperature | % activated O:2 |
|---|---|---|
| Sodium acetate pH 4.5 | 30° C. | 65.8 |
| Sodium acetate pH 4.5 | 50° C. | 65.4 |
| Sodium acetate pH 4.5 | 60° C. | 68.3 |
| MES pH 6.0 | 30° C. | 43.9 |
| Phosphate pH 8.0 | 30° C. | 26.2 |

Derivation of *S. Typhimurium* O-antigen-core with ADH by Reductive Amination Comparing Different Reaction Conditions (Table 4).

Reaction conditions described in this application (Table 4, method 1) for performing the reductive amination with ADH were compared with the traditional method reported in literature [13] (Table 4, method 2), working with *S. Typhimurium* O-antigen-core (strain D23580). Results are summarized in Table 5, showing that the process at lower pH is faster and also more efficient.

TABLE 4

Reaction conditions used for performing reductive amination with ADH comparing NVGH procedure with the classical procedure reported in literature.

| Method | OAg (mg/mL) | ADH (mg/mL) | $NaBH_3CN$ (mg/mL) | Buffer | Temperature (° C.) |
|---|---|---|---|---|---|
| 1 | 40 | 48 | 48 | AcONa 100 mM pH 4.5 | 30 |
| 2 | 20 | 100 | 100 | $NaHCO_3$ 100 mM pH 8.3 | 37 |

TABLE 5

Reductive amination of O:4,5-KDO with ADH using method 1 is more efficient and faster than using the classical method reported in literature (method 2).

| Method | Reaction time | % activated O:4,5 |
|---|---|---|
| 1 | 3 h | 88 |
| 2 | 3 h | 31.6 |
| 2 | 24 h | 28.5 |
| 2 | 5 d | 28.5 |

REFERENCES

[1] Watson et al. (1992) *Infect Immun.* 60(11):4679-86
[2] Konadu et al. (1996) *Infect Immun.* (7):2709-15.
[3] Petri et al. (2008) *J Clin Invest.* 118(4):1277-90.
[4] Ashkenazi et al. (1999) *J Infect Dis.* 179(6):1565-8
[5] Cohen et al. (1997) *Lancet* 349(9046):155-9
[6] Passwell et al. (2003) *Pediatr Infect Dis J.* 22(8):701-6
[7] Pozsgay et al. (2007) *Proc Natl Acad Sci USA.* 104(36): 14478-82
[8] Robbins et al. (2009) *Proc Natl Acad Sci USA.* 106(19): 7974-8
[9] Taylor et al. (1993) *Infect Immun.* 61(9):3678-87
[10] Konadu et al. (1994) *Infect Immun.* 62(11):5048-54.
[11] Ahmed et al. (2006) J Infect Dis. 193(4):515-21
[12] Cox et al. (2011) Glycoconj J 28:165-182
[13] Chu et al. (1991) *Infect Immun.* 59(12):4450-58.
[14] WO96/40242.
[15] Lei et al. (2000) *Dev Biol (Basel)* 103:259-264.
[16] WO00/38711; U.S. Pat. No. 6,146,902.
[17] Westphal and Jann (1965) *Methods Carbohydr. Chem.* 5:83-91.
[18] Micoli et al., 2012 PlosOne, in press.
[19] Knirel et al. (2011) Glycobiology. (10) 1362-72,
[20] Chhibber et al. (2005) Indian *J Exp Biol.* 43(1):40-5
[21] Gupta et al. (1992) *Infect Immun.* 60(8):3201-8
[22] Cox et al. (2005) *Vaccine.* 23(43):5045-54
[23] Lemercinier and Jones (1996) *Carbohydrate Res.* 296: 83-96.
[24] Hestrin (1994) *J Biol Chem* 180(1):249-61.
[25] Kao and Tasi (2004) *Vaccine.* 22(3-4):335-44
[26] Ramsay et al. (2001) *Lancet* 357(9251):195-196.
[27] Lindberg (1999) *Vaccine* 17 Suppl 2:S28-36.
[28] Buttery & Moxon (2000) *J R Coll Physicians Lond* 34:163-168.
[29] Ahmad & Chapnick (1999) *Infect Dis Clin North Am* 13:113-33, vii.
[30] Goldblatt (1998) *J. Med Microblol.* 47:563-567.
[31] European patent 0477508.

[32] U.S. Pat. No. 5,306,492.
[33] WO98/42721.
[34] Dick et al. in *Conjugate Vaccines* (eds. Cruse et al.) Karger, Basel, 1989, 10:48-114.
[35] Hermanson *Bioconjugate Techniques*, Academic Press, San Diego (1996) ISBN: 0123423368.
[36] *Research Disclosure,* 453077 (January 2002)
[37] EP-A-0372501.
[38] EP-A-0378881.
[39] EP-A-0427347.
[40] WO93/17712
[41] WO94/03208.
[42] WO98/58668.
[43] EP-A-0471177.
[44] WO91/01146
[45] Falugi et al. (2001) *Eur J Immunol* 31:3816-3824.
[46] Baraldo et al. (2004) *Infect Immun* 72(8):4884-7.
[47] EP-A-0594610.
[48] Ruan et al. (1990) *J Immunol* 145:3379-3384.
[49] WO00/56360.
[50] Kuo et al. (1995) *Infect Immun* 63:2706-13.
[51] Michon et al. (1998) *Vaccine.* 16:1732-41.
[52] WO02/091998.
[53] WO01/72337
[54] WO00/61761.
[55] WO00/33882
[56] WO99/42130
[57] Canh et al. (2004) *Infect Immun.* 72(11):6586-8
[58] Rondini et al. (2011) Clin Vaccine Immunol. 18(3): 460-8
[59] Micoli et al. (2011) *Vaccine.* 29(4):712-20
[60] WO 2009/150543
[61] Watson (2000) *Pediatr Infect Dis J* 19:331-332.
[62] Rubin (2000) *Pediatr Clin North Am* 47:269-285, v.
[63] Jedrzejas (2001) *Microbiol Mol Biol Rev* 65:187-207.
[64] *Vaccines* (2004) eds. Plotkin & Orenstein. ISBN 0-7216-9688-0.
[65] Bell (2000) *Pediatr Infect Dis J* 19:1187-1188.
[66] Iwarson (1995) *APMIS* 103:321-326.
[67] Gerlich et al. (1990) *Vaccine* 8 Suppl:S63-68 & 79-80.
[68] Hsu et al. (1999) *Clin Liver Dis* 3:901-915.
[69] Gustafsson et al. (1996) *N. Engl. J. Med.* 334:349-355.
[70] Rappuoli et al. (1991) *TIBTECH* 9:232-238.
[71] WO02/02606.
[72] Kalman et al. (1999) *Nature Genetics* 21:385-389.
[73] Read et al. (2000) *Nucleic Acids Res* 28:1397-406.
[74] Shirai et al. (2000) *J. Infect. Dis.* 181(Suppl 3):S524-S527.
[75] WO99/27105.
[76] WO00/27994.
[77] WO00/37494.
[78] WO99/28475.
[79] Ross et al. (2001) *Vaccine* 19:4135-4142.
[80] Sutter et al. (2000) *Pediatr Clin North Am* 47:287-308.
[81] Zimmerman & Spann (1999) *Am Fam Physician* 59:113-118, 125-126.
[82] Dreesen (1997) *Vaccine* 15 Suppl:S2-6.
[83] *MMWR Morb Mortal Wkly Rep* 1998 Jan. 16; 47(1):12, 19.
[84] McMichael (2000) *Vaccine* 19 Suppl 1:S101-107.
[85] WO02/34771.
[86] Dale (1999) *Infect Dis Clin North Am* 13:227-43, viii.
[87] Ferretti et al. (2001) *PNAS USA* 98: 4658-4663.
[88] WO03/093306.
[89] WO2004/018646.
[90] WO2004/041157.
[91] Ichiman and Yoshida (1981) *J. Appl. Bacteriol.* 51:229.
[92] U.S. Pat. No. 4,197,290
[93] Ichiman et al. (1991) *J. Appl. Bacteriol.* 71:176.
[94] Robinson & Torres (1997) *Seminars in Immunology* 9:271-283.
[95] Donnelly et al. (1997) *Annu Rev Immunol* 15:617-648.
[96] Scott-Taylor & Dalgleish (2000) *Expert Opin Investig Drugs* 9:471-480.
[97] Apostolopoulos & Plebanski (2000) *Curr Opin Mol Ther* 2:441-447.
[98] Han (1999) *Curr Opin Mol Ther* 1:116-120.
[99] Dubensky et al. (2000) *Mol Med* 6:723-732.
[100] Robinson & Pertmer (2000) *Adv Virus Res* 55:1-74.
[101] Donnelly et al. (2000) *Am J Respir Crit Care Med* 162(4 P 2):S190-193.
[102] Davis (1999) *Mt. Sinai Med.* 66:84-90.
[103] Paoletti et al. (2001) *Vaccine* 19:2118-2126.
[104] WO00/56365.
[105] Gennaro (2000) *Remington: The Science and Practice of Pharmacy.* 20th edition, ISBN: 0683306472.
[106] WO03/009869.
[107] Almeida & Alpar (1996) *J. Drug Targeting* 3:455-467.
[108] Agarwal & Mishra (1999) *Indian J Exp Biol* 37:6-16.
[109] WO00/53221.
[110] Jakobsen et al. (2002) *Infect Immun* 70:1443-1452.
[111] Bergquist et al. (1998) *APMIS* 106:800-806.
[112] Baudner et al. (2002) *Infect Immun* 70:4785-4790.
[113] Ugozzoli et al. (2002) *J Infect Dis* 186:1358-1361.
[114] WO90/14837.
[115] Podda & Del Giudice (2003) *Expert Rev Vaccines* 2:197-203.
[116] Podda (2001) *Vaccine* 19: 2673-2680.
[117] *Vaccine Design: The Subunit and Adjuvant Approach* (eds. Powell & Newman) Plenum Press 1995 (ISBN 0-306-44867-X).
[118] *Vaccine Adjuvants: Preparation Methods and Research Protocols* (Volume 42 of *Methods in Molecular Medicine* series). ISBN: 1-59259-083-7. Ed. O'Hagan.
[119] Allison & Byars (1992) *Res Immunol* 143:519-25.
[120] Hariharan et al. (1995) *Cancer Res* 55:3486-9.
[121] US-2007/014805.
[122] WO95/11700.
[123] U.S. Pat. No. 6,080,725.
[124] WO2006/113373.
[125] WO2005/097181.
[126] U.S. Pat. No. 5,057,540.
[127] WO96/33739.
[128] EP-A-0109942.
[129] WO96/1711.
[130] WO00/07621.
[131] Barr et al. (1998) *Advanced Drug Delivery Reviews* 32:247-271.
[132] Sjolanderet et al. (1998) *Advanced Drug Delivery Reviews* 32:321-338.
[133] EP-A-0689454.
[134] Johnson et al. (1999) *Bioorg Med Chem Lett* 9:2273-2278.
[135] Evans et al. (2003) *Expert Rev Vaccines* 2:219-229.
[136] Meraldi et at (2003) *Vaccine* 21:2485-2491.
[137] Pajak et al. (2003) *Vaccine* 21:836-842.
[138] Kandimalla et al. (2003) *Nucleic Acids Research* 31:2393-2400.
[139] WO02/26757.
[140] WO99/62923.
[141] Krieg (2003) *Nature Medicine* 9:831-835.
[142] McCluskie et al. (2002) *FEMS Immunology and Medical Microbiology* 32:179-185.
[143] WO98/40100.

[144] U.S. Pat. No. 6,207,646.
[145] U.S. Pat. No. 6,239,116.
[146] U.S. Pat. No. 6,429,199.
[147] Kandimalla et al. (2003) *Biochemical Society Transactions* 31 (part 3):654-658.
[148] Blackwell et al. (2003) *J Immunol* 170:4061-4068.
[149] Krieg (2002) *Trends Immunol* 23:64-65.
[150] WO01/95935.
[151] Kandimalla et al. (2003) *BBRC* 306:948-953.
[152] Bhagat et al. (2003) *BBRC* 300:853-861.
[153] WO03/035836.
[154] Schellack et al. (2006) *Vaccine* 24:5461-72.
[155] Lingnau et al. (2007) *Expert Rev Vaccines* 6:741-6.
[156] WO2004/084938.
[157] WO95/17211.
[158] WO98/42375.
[159] Beignon et al. (2002) *Infect Immun* 70:3012-3019.
[160] Pizza et al. (2001) *Vaccine* 19:2534-2541.
[161] Pizza et al. (2000) *Int J Med Microbiol* 290:455-461.
[162] Scharton-Kersten et al. (2000) *Infect Immun* 68:5306-5313.
[163] Ryan et al. (1999) *Infect Immun* 67:6270-6280.
[164] Partidos et al. (1999) *Immunol Lett* 67:209-216.
[165] Peppoloni et al. (2003) *Expert Rev Vaccines* 2:285-293.
[166] Pine et al. (2002) *J Control Release* 85:263-270.
[167] Tebbey et at (2000) *Vaccine* 18:2723-34.
[168] Domenighini et al. (1995) *Mol Microbiol* 15:1165-1167.
[169] WO99/40936.
[170] WO99/44636.
[171] Singh et al. (2001) *J Cont Release* 70:267-276.
[172] WO99/27960.
[173] U.S. Pat. No. 6,090,406.
[174] U.S. Pat. No. 5,916,588.
[175] EP-A-0626169.
[176] Stanley (2002) *Clin Exp Dermatol* 27:571-577.
[177] Jones (2003) *Curr Opin Investig Drugs* 4:214-218.
[178] WO99/11241.
[179] WO94/00153.
[180] WO98/57659.
[181] European patent applications 0835318, 0735898 and 0761231.
[182] Gennaro (2000) *Remington: The Science and Practice of Pharmacy.* 20th edition, ISBN: 0613306472.
[183] *Methods In Enzymology* (S. Colowick and N. Kaplan, eds., Academic Press, Inc.)
[184] *Handbook of Experimental Immunology*, Vols. I-IV (D. M. Weir and C. C. Blackwell, eds, 1986, Blackwell Scientific Publications)
[185] Sambrook et al. (2001) *Molecular Cloning: A Laboratory Manual,* 3rd edition (Cold Spring Harbor Laboratory Press).
[186] *Handbook of Surface and Colloidal Chemistry* (Birdi, K. S. ed., CRC Press, 1997)
[187] Ausubel et al. (eds) (2002) *Short protocols in molecular biology,* 5th edition (Current Protocols).
[188] *Molecular Biology Techniques: An Intensive Laboratory Course,* (Ream et al., eds., 1998, Academic Press)
[189] *PCR (Introduction to Biotechniques Series).* 2nd ed. (Newton & Graham eds., 1997, Springer Verlag)
[190] Geysen et al. (1984) *PNAS USA* 81:3998-4002.
[191] Carter (1994) *Methods Mol Biol* 36:207-23.
[192] Jameson, B A et al. 1988, *CABIOS* 4(1):181-186.
[193] Raddrizzani & Hammer (2000) *Brief Bioinform* 1(2): 179-89.
[194] Bublil et al. (2007) *Proteins* 68(1):294-304.
[195] De Lalla et al. (1999) *J. Immunol.* 163:1725-29.
[196] Kwok et al. (2001) *Trends Immunol* 22:583-88.
[197] Brusic et al. (1998) *Bioinformatics* 14(2):121-30
[198] Meister et al. (1995) *Vaccine* 13(6):581-91.
[199] Roberts et al. (1996) *AIDS Res Hum Retroviruses* 12(7):593-610.
[200] Maksyutov & Zagrebelnaya (1993) *Comput Appl Biosci* 9(3):291-7.
[201] Feller & de la Cruz (1991) *Nature* 349(6311):720-1.
[202] Hopp (1993) *Peptide Research* 6:183-190.
[203] Welling et al. (1985) *FEBS Lett.* 188:215-218.
[204] Davenport et al. (1995) *Immunogenetics* 42:392-297.
[205] Tsurui & Takahashi (2007) *J Pharmacol Sci.* 105(4): 299-316.
[206] Tong et al. (2007) *Brief Bioinform.* 8(2):96-108.
[207] Schirle et al. (2001) *J Immunol Methods.* 257(1-2): 1-16.
[208] Chen et al. (2007) *Amino Acids* 33(3):423-8.
[209] Dubois et al. (1956) *Analytical Chemistry* 28:350.

We claim:

1. A process for coupling a polysaccharide to a linker, comprising:
combining the polysaccharide with an additional linker comprising a primary amine group in the presence of a reducing agent, wherein the polysaccharide comprises a carbonyl group at the reducing terminus,
reacting the carbonyl group with the primary amine group by reductive amination to form a polysaccharide-additional linker intermediate, wherein the reductive amination is carried out at a pH between 4 and 5,
coupling the polysaccharide-additional linker intermediate to the linker, to form a polysaccharide-linker compound, and
precipitating unreacted linker under aqueous conditions at a pH of less than 5.

2. The process of claim 1, wherein the polysaccharide comprises a core domain from a lipopolysaccharide of a Gram-negative bacterium, and an O-antigen from a lipopolysaccharide of a Gram-negative bacterium linked to the core domain.

3. The process of claim 2, wherein the lipopolysaccharide is from a *Salmonella* bacterium.

4. The process of claim 3, wherein the lipopolysaccharide is from *S. Paratyphi* A, *S. Typhimurium* or *S. Enteritidis*.

5. The process of claim 1, wherein the polysaccharide is a bacterial capsular polysaccharide.

6. The process of claim 5, wherein the bacterial capsular polysaccharide is from *N. meningitidis* serogroup X.

7. The process of claim 1, wherein the reductive amination comprises reacting the carbonyl group with $Y_1$ in the additional linker having the formula $Y_1$-L-$Y_2$, to form the polysaccharide-additional linker intermediate compound in which the polysaccharide is coupled to the additional linker via a C—N linkage, wherein: $Y_1$ comprises a primary amine group that can react with the carbonyl group in the polysaccharide; $Y_2$ comprises a second reactive group; and L is a linking moiety.

8. The process of claim 7, wherein the $Y_1$ and $Y_2$ are both —$NHNH_2$ groups.

9. The process of claim 7, wherein L has formula -L'-$L^2$-L'-, where L' is carbonyl and $L^2$ is a straight chain alkyl with 1 to 10 carbon atoms.

10. The process of claim 8, wherein $L^2$ is —$(CH_2)_4$—.

11. The process of claim 8, wherein L is carbonyl.

12. The process of claim 7, wherein $Y_2$ comprises a primary amine group.

13. The process of claim 7, wherein $Y_2$ comprises a —SH group.

\* \* \* \* \*